(12) United States Patent
Abbas et al.

(10) Patent No.: US 10,316,306 B2
(45) Date of Patent: Jun. 11, 2019

(54) THERMOSTABLE ALPHA AMYLASE

(71) Applicant: DSM IP ASSETS B.V., Heerlen (NL)

(72) Inventors: Hanna Elisabet Abbas, Echt (NL); Jan Metske Van Der Laan, Echt (NL); Johannes Gustaaf Ernst Van Leeuwen, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 34 days.

(21) Appl. No.: 15/501,149

(22) PCT Filed: Aug. 6, 2015

(86) PCT No.: PCT/EP2015/068162
§ 371 (c)(1),
(2) Date: Feb. 1, 2017

(87) PCT Pub. No.: WO2016/020478
PCT Pub. Date: Feb. 11, 2016

(65) Prior Publication Data
US 2017/0260514 A1    Sep. 14, 2017

(30) Foreign Application Priority Data
Aug. 7, 2014  (EP) .................................. 14180205

(51) Int. Cl.
| | |
|---|---|
| *C12N 9/12* | (2006.01) |
| *C12N 15/00* | (2006.01) |
| *C12N 1/20* | (2006.01) |
| *C07H 21/04* | (2006.01) |
| *C12N 9/30* | (2006.01) |
| *A21D 2/26* | (2006.01) |

(52) U.S. Cl.
CPC ............... *C12N 9/242* (2013.01); *A21D 2/26* (2013.01); *C12Y 302/01001* (2013.01)

(58) Field of Classification Search
None
See application file for complete search history.

(56) References Cited

U.S. PATENT DOCUMENTS 5,059,430 A * 10/1991 Bowles .................. A21D 8/042
426/20
2014/0127753 A1    5/2014  Fukuyama et al.
2015/0064765 A1 *  3/2015  Roubos ................... C12P 21/02
435/203

FOREIGN PATENT DOCUMENTS

WO      2013/160316 A1     10/2013
WO      WO-2013160316 A1 * 10/2013  .............. C12P 21/02

OTHER PUBLICATIONS

International Search Report of PCT/EP2015/068162 dated Sep. 15, 2015.

* cited by examiner

*Primary Examiner* — Yong D Pak
(74) *Attorney, Agent, or Firm* — McBee Moore Woodward & Vanik IP, LLC; Susan McBee; Chester Moore

(57) ABSTRACT

The present invention relates to an alpha amylase enzyme and to its use in the food, feed and non-food industry.

16 Claims, 5 Drawing Sheets
Specification includes a Sequence Listing.

```
MVKSILASVF FAATALAATP AEWRSQSIYF LLTDRFARTD GSTTAACDTS DRKYCGGTWQ    60
GIINHLDYIQ GMGFTAIWIS PVTEQLPQDT GYGEAYHGYW QQDIYSLNSN FGTADDLKAL   120
SSALHARGMY LMVDVVANHM GYAGAGSSVD YSVFNPFNSQ SYFHPYCLIT DYNNQTNVED   180
CWLGDNTVSL PDLRTEDSDV QNIWYDWIKE LVSNYSIDGL RIDTVKHVQK DFWPGYNDAA   240
GVYCVGEVFD GDPAYTCPYQ NYLDGVLNYP IYYPLLRAFQ STSGSISDLY NMINTVKSDC   300
ADPTLLGTFI ENHDNPRFAS YTSDISLAKN AIAFTILSDG IPIIYYGQEQ HYSGGNDPAN   360
REALWLSGYS TTSELYKLIA TLNKIRNHAI SKDSGYLTYK NYPIYQDSNT IAMRKGTDGS   420
QVITVLSNLG ASGSSYTLSL SGTGYTAGQK LTEIYTCTTV TVDSSGNVPV PMASGLPRVL   480
YPASKLSGSG LCSSS                                                   495
```

```
MVKSILASVF FAATALAATP AEWRSQSIYF LLTDRFARTD GSTTAACDTS DRKYCGGTWQ      60
GIINHLDYIQ GMGFTAIWIS PVTEQLPQDT GYGEAYHGYW QQDIYSLNSN FGTADDLKAL     120
SSALHARGMY LMVDVVANHM GYAGAGSSVD YSVFNPFNSQ SYFHPYCLIT DYNNQTNVED     180
CWLGDNTVSL PDLRTEDSDV QNIWYDWIKE LVSNYSIDGL RIDTVKHVQK DFWPGYNDAA     240
GVYCVGEVFD GDPAYTCPYQ NYLDGVLNYP IYYPLLRAFQ STSGSISDLY NMINTVKSDC     300
ADPTLLGTFI ENHDNPRFAS YTSDISLAKN AIAFTILSDG IPIIYYGQEQ HYSGGNDPAN     360
REALWLSGYS TTSELYKLIA TLNKIRNHAI SKDSGYLTYK NYPIYQDSNT IAMRKGTDGS     420
QVITVLSNLG ASGSSYTLSL SGTGYTAGQK LTEIYTCTTV TVDSSGNVPV PMASGLPRVL     480
YPASKLSGSG LCSSS                                                     495
```

FIG.1

```
atggtcaagt ccatcctggc ctccgtcttc ttcgctgcca ctgctcttgc tgccactcct    60
gctgaatggc gctcccagtc catctacttc ctgctcaccg accgcttcgc tcgtaccgat   120
ggcagcacca ctgctgcctg cgacacctcc gaccgcaagt actgcggtgg tacctggcag   180
ggtatcatca accacctcga ctacatccag ggtatgggtt tcactgccat ctggatatct   240
cctgtgaccg agcagcttcc tcaggacacc ggatacggtg aggcctacca cggatactgg   300
cagcaggata tctactctct gaactccaac ttcggtactg ccgatgacct caaggccctc   360
agctctgctc tgcacgctcg tggaatgtac ctgatggttg acgttgttgc caaccacatg   420
ggctacgctg gtgctggaag ctctgttgac tactccgtct caacccctt caacagccag    480
tcctacttcc accctactg cttgatcacc gactacaaca accagaccaa cgtcgaggac    540
tgctggctcg gtgacaacac cgtgtctctt cccgatctcc gcaccgaaga ctcggatgtc   600
cagaacatct ggtacgactg gatcaaggag cttgtctcca actactccat tgatggtctg   660
cgtatcgaca ccgtcaagca cgtccagaag gacttctggc ccggctacaa cgatgctgct   720
ggtgtctact gcgttggtga agtcttcgat ggtgaccctg cctacacctg cccctaccag   780
aactaccttg atggtgtcct gaactacccc atctactacc ccttgctccg tgctttccag   840
agcacttctg gctccatctc cgatctgtac aacatgatca cactgtcaa gtccgactgc    900
gcggacccca ctctccttgg taccttcatt gagaaccacg acaaccctcg tttcgcctcc   960
tacaccagcg atatctccct ggccaagaac gccattgctt tcaccatcct gtcggatggc  1020
attcccatta tctactacgg ccaggagcag cactactctg gtggtaacga ccctgccaac  1080
cgtgaggctc tctggctatc cggatacagc accacctcgg agctctacaa gttgattgcc  1140
accctcaaca agatccgcaa ccacgccatc tccaaggact ctggctacct gacctacaag  1200
aactatccca tctaccagga cagcaacacc attgccatgc gcaagggcac cgatggctcc  1260
caggtcatca ccgtcctctc caaccttggt gcctccggca gcagctacac cctctccctc  1320
tccggcactg gctacactgc tggccagaag ctcaccgaga tctacacttg caccaccgtc  1380
actgttgact cttctggcaa cgtccccgtg cccatggcct ccggtctgcc ccgtgtcctc  1440
tacccccgcct ccaagctgtc tggctccggt ctttgctcga gctcataa               1488
```

FIG. 2

```
MVKSILASVF FAATALAATP ADWRSQSIYF LLTDRFARTD GSTTATCNTA DQKYCGGTWQ    60
GIIDKLDYIQ GMGFTAIWIT PVTAQLPQTT AYGDAYHGYW QQDIYSLNEN YGTADDLKAL   120
SSALHERGMY LMVDVVANHM GYDGAGSSVD YSVFKPFSSQ DYFHPFCFIQ NYEDQTQVED   180
CWLGDNTVSL PDLDTTKDVV KNEWYDWVGS LVSNYSIDGL RIDTVKHVQK DFWPGYNKAA   240
GVYCIGEVLD GDPAYTCPYQ NVMDGVLNYP IYYPLLNAFK STSGSMDDLY NMINTVKSDC   300
PDSTLLGTFV ENHDNPRFAS YTNDIALAKN VAAFIILNDG IPIIYAGQEQ HYAGGNDPAN   360
REATWLSGYP TDSELYKLIA SANAIRNYAI SKDTGFVTYK NWPIYKDDTT IAMRKGTDGS   420
QIVTILSNKG ASGDSYTLSL SGAGYTAGQQ LTEVIGCTTV TVGSDGNVPV PMAGGLPRVL   480
YPTEKLAGSK ICSSS                                                   495
```

FIG. 3

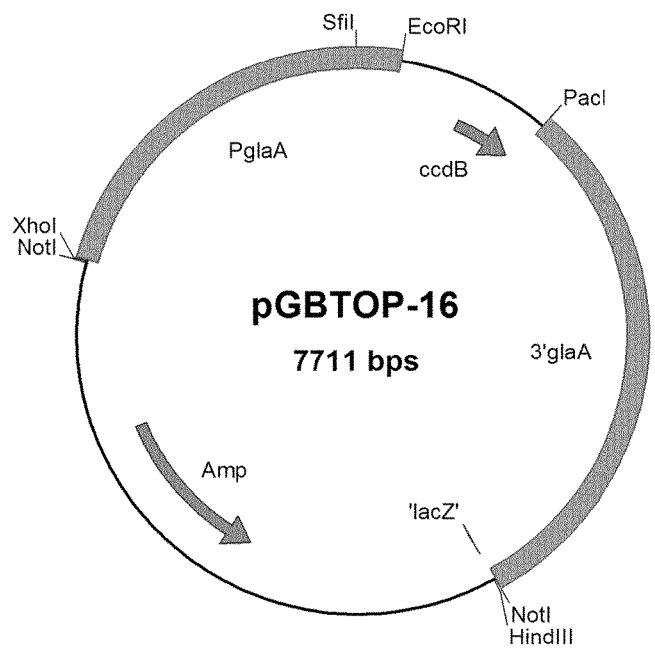

FIG. 4

SEQUENCE LISTING

```
<160> NUMBER OF SEQ ID NOS: 3

<210> SEQ ID NO 1
<211> LENGTH: 495
<212> TYPE: PRT
<213> ORGANISM: Artificial Sequence
<220> FEATURE:
<223> OTHER INFORMATION: AMY1 polypeptide sequence
<220> FEATURE:
<221> NAME/KEY: SIGNAL
<222> LOCATION: (1)..(17)

<400> SEQUENCE: 1

Met Val Lys Ser Ile Leu Ala Ser Val Phe Phe Ala Ala Thr Ala Leu
1               5                   10                  15

Ala Ala Thr Pro Ala Glu Trp Arg Ser Gln Ser Ile Tyr Phe Leu Leu
                20                  25                  30

Thr Asp Arg Phe Ala Arg Thr Asp Gly Ser Thr Thr Ala Ala Cys Asp
            35                  40                  45

Thr Ser Asp Arg Lys Tyr Cys Gly Gly Thr Trp Gln Gly Ile Ile Asn
        50                  55                  60

His Leu Asp Tyr Ile Gln Gly Met Gly Phe Thr Ala Ile Trp Ile Ser
65                  70                  75                  80

Pro Val Thr Glu Gln Leu Pro Gln Asp Thr Gly Tyr Gly Glu Ala Tyr
                85                  90                  95

His Gly Tyr Trp Gln Gln Asp Ile Tyr Ser Leu Asn Ser Asn Phe Gly
                100                 105                 110
```

```
Thr Ala Asp Asp Leu Lys Ala Leu Ser Ser Ala Leu His Ala Arg Gly
            115                 120                 125

Met Tyr Leu Met Val Asp Val Ala Asn His Met Gly Tyr Ala Gly
130                 135                 140

Ala Gly Ser Ser Val Asp Tyr Ser Val Phe Asn Pro Phe Asn Ser Gln
145                 150                 155                 160

Ser Tyr Phe His Pro Tyr Cys Leu Ile Thr Asp Tyr Asn Asn Gln Thr
                165                 170                 175

Asn Val Glu Asp Cys Trp Leu Gly Asp Asn Thr Val Ser Leu Pro Asp
            180                 185                 190

Leu Arg Thr Glu Asp Ser Asp Val Gln Asn Ile Trp Tyr Asp Trp Ile
        195                 200                 205

Lys Glu Leu Val Ser Asn Tyr Ser Ile Asp Gly Leu Arg Ile Asp Thr
    210                 215                 220

Val Lys His Val Gln Lys Asp Phe Trp Pro Gly Tyr Asn Asp Ala Ala
225                 230                 235                 240

Gly Val Tyr Cys Val Gly Glu Val Phe Asp Gly Asp Pro Ala Tyr Thr
                245                 250                 255

Cys Pro Tyr Gln Asn Tyr Leu Asp Gly Val Leu Asn Tyr Pro Ile Tyr
            260                 265                 270

Tyr Pro Leu Leu Arg Ala Phe Gln Ser Thr Ser Gly Ser Ile Ser Asp
        275                 280                 285

Leu Tyr Asn Met Ile Asn Thr Val Lys Ser Asp Cys Ala Asp Pro Thr
    290                 295                 300

Leu Leu Gly Thr Phe Ile Glu Asn His Asp Asn Pro Arg Phe Ala Ser
305                 310                 315                 320

Tyr Thr Ser Asp Ile Ser Leu Ala Lys Asn Ala Ile Ala Phe Thr Ile
                325                 330                 335

Leu Ser Asp Gly Ile Pro Ile Ile Tyr Tyr Gly Gln Glu Gln His Tyr
            340                 345                 350

Ser Gly Gly Asn Asp Pro Ala Asn Arg Glu Ala Leu Trp Leu Ser Gly
        355                 360                 365

Tyr Ser Thr Thr Ser Glu Leu Tyr Lys Leu Ile Ala Thr Leu Asn Lys
    370                 375                 380

Ile Arg Asn His Ala Ile Ser Lys Asp Ser Gly Tyr Leu Thr Tyr Lys
385                 390                 395                 400

Asn Tyr Pro Ile Tyr Gln Asp Ser Asn Thr Ile Ala Met Arg Lys Gly
                405                 410                 415

Thr Asp Gly Ser Gln Val Ile Thr Val Leu Ser Asn Leu Gly Ala Ser
            420                 425                 430

Gly Ser Ser Tyr Thr Leu Ser Leu Ser Gly Thr Gly Tyr Thr Ala Gly
        435                 440                 445

Gln Lys Leu Thr Glu Ile Tyr Thr Cys Thr Thr Val Thr Val Asp Ser
    450                 455                 460

Ser Gly Asn Val Pro Val Pro Met Ala Ser Gly Leu Pro Arg Val Leu
465                 470                 475                 480

Tyr Pro Ala Ser Lys Leu Ser Gly Ser Gly Leu Cys Ser Ser Ser
                485                 490                 495

<210> SEQ ID NO 2
<211> LENGTH: 1488
<212> TYPE: DNA
<213> ORGANISM: Artificial Sequence
<220> FEATURE:
<223> OTHER INFORMATION: polynucleotide sequence encoding the amino acid
``` sequence of SEQ ID NO:1, codon-optimized for expression in Aspergillus niger

<400> SEQUENCE: 2

```
atggtcaagt ccatcctggc ctccgtcttc ttcgctgcca ctgctcttgc tgccactcct      60
gctgaatggc gctcccagtc catctacttc ctgctcaccg accgcttcgc tcgtaccgat     120
ggcagcacca ctgctgcctg cgacacctcc gaccgcaagt actgcggtgg tacctggcag     180
ggtatcatca ccaccctcga ctacatccag ggtatgggtt tcactgccat ctggatatct     240
cctgtgaccg agcagcttcc tcaggacacc ggatacggtg aggcctacca cggatactgg     300
cagcaggata tctactctct gaactccaac ttcggtactg ccgatgacct caaggccctc     360
agctctgctc tgcacgctcg tggaatgtac ctgatggttg acgttgttgc aaccacatg      420
ggctacgctg tgctggaag ctctgttgac tactccgtct tcaaccccctt caacagccag     480
tcctacttcc accctactg cttgatcacc gactacaaca accagaccaa cgtcgaggac      540
tgctggctcg tgacaacac cgtgtctctt cccgatctcc gcaccgaaga ctcggatgtc      600
cagaacatct ggtacgactg gatcaaggag cttgtctcca actactccat tgatggtctg     660
cgtatcgaca ccgtcaagca cgtccagaag gacttctggc ccggctacaa cgatgctgct     720
ggtgtctact gcgttggtga agtcttcgat ggtgaccctg cctacacctg ccctaccag      780
aactaccttg atggtgtcct gaactacccc atctactacc ccttgctccg tgctttccag     840
agcacttctg gctccatctc cgatctgtac aacatgatca cactgtcaa gtccgactgc      900
gcggaccca ctctccttgg taccttcatt gagaaccacg caaccctcg tttcgcctcc       960
tacaccagcg atatctccct ggccaagaac gccattgctt tcaccatcct gtcggatggc    1020
attcccatta tctactacgg ccaggagcag cactactctg gtggtaacga ccctgccaac    1080
cgtgaggctc tctggctatc cggatacagc accacctcgg agctctacaa gttgattgcc    1140
accctcaaca agatccgcaa ccacgccatc tccaaggact ctggctacct gacctacaag    1200
aactatccca tctaccagga cagcaacacc attgccatgc gcaagggcac cgatggctcc    1260
caggtcatca ccgtcctctc caaccttggt gcctccggca gcagctacac cctctcccctc   1320
tccggcactg gctacactgc tggccagaag ctcaccgaga tctacacttg caccaccgtc    1380
actgttgact cttctggcaa cgtccccgtg cccatggcct ccggtctgcc ccgtgtcctc    1440
tacccccgcct ccaagctgtc tggctccggt ctttgctcga gctcataa               1488
```

<210> SEQ ID NO 3
<211> LENGTH: 495
<212> TYPE: PRT
<213> ORGANISM: Aspergillus niger

<400> SEQUENCE: 3

```
Met Val Lys Ser Ile Leu Ala Ser Val Phe Phe Ala Ala Thr Ala Leu
1               5                  10                  15

Ala Ala Thr Pro Ala Asp Trp Arg Ser Gln Ser Ile Tyr Phe Leu Leu
            20                  25                  30

Thr Asp Arg Phe Ala Arg Thr Asp Gly Ser Thr Thr Ala Thr Cys Asn
        35                  40                  45

Thr Ala Asp Gln Lys Tyr Cys Gly Gly Thr Trp Gln Gly Ile Ile Asp
    50                  55                  60

Lys Leu Asp Tyr Ile Gln Gly Met Gly Phe Thr Ala Ile Trp Ile Thr
65                  70                  75                  80

Pro Val Thr Ala Gln Leu Pro Gln Thr Thr Ala Tyr Gly Asp Ala Tyr
```

```
                      85                  90                  95
His Gly Tyr Trp Gln Gln Asp Ile Tyr Ser Leu Asn Glu Asn Tyr Gly
                100                 105                 110

Thr Ala Asp Asp Leu Lys Ala Leu Ser Ser Ala Leu His Glu Arg Gly
            115                 120                 125

Met Tyr Leu Met Val Asp Val Ala Asn His Met Gly Tyr Asp Gly
        130                 135                 140

Ala Gly Ser Ser Val Asp Tyr Ser Val Phe Lys Pro Phe Ser Ser Gln
145                 150                 155                 160

Asp Tyr Phe His Pro Phe Cys Phe Ile Gln Asn Tyr Glu Asp Gln Thr
                165                 170                 175

Gln Val Glu Asp Cys Trp Leu Gly Asp Asn Thr Val Ser Leu Pro Asp
            180                 185                 190

Leu Asp Thr Thr Lys Asp Val Val Lys Asn Glu Trp Tyr Asp Trp Val
        195                 200                 205

Gly Ser Leu Val Ser Asn Tyr Ser Ile Asp Gly Leu Arg Ile Asp Thr
    210                 215                 220

Val Lys His Val Gln Lys Asp Phe Trp Pro Gly Tyr Asn Lys Ala Ala
225                 230                 235                 240

Gly Val Tyr Cys Ile Gly Glu Val Leu Asp Gly Asp Pro Ala Tyr Thr
                245                 250                 255

Cys Pro Tyr Gln Asn Val Met Asp Gly Val Leu Asn Tyr Pro Ile Tyr
            260                 265                 270

Tyr Pro Leu Leu Asn Ala Phe Lys Ser Thr Ser Gly Ser Met Asp Asp
        275                 280                 285

Leu Tyr Asn Met Ile Asn Thr Val Lys Ser Asp Cys Pro Asp Ser Thr
    290                 295                 300

Leu Leu Gly Thr Phe Val Glu Asn His Asp Asn Pro Arg Phe Ala Ser
305                 310                 315                 320

Tyr Thr Asn Asp Ile Ala Leu Ala Lys Asn Val Ala Ala Phe Ile Ile
                325                 330                 335

Leu Asn Asp Gly Ile Pro Ile Ile Tyr Ala Gly Gln Glu Gln His Tyr
            340                 345                 350

Ala Gly Gly Asn Asp Pro Ala Asn Arg Glu Ala Thr Trp Leu Ser Gly
        355                 360                 365

Tyr Pro Thr Asp Ser Glu Leu Tyr Lys Leu Ile Ala Ser Ala Asn Ala
    370                 375                 380

Ile Arg Asn Tyr Ala Ile Ser Lys Asp Thr Gly Phe Val Thr Tyr Lys
385                 390                 395                 400

Asn Trp Pro Ile Tyr Lys Asp Asp Thr Thr Ile Ala Met Arg Lys Gly
                405                 410                 415

Thr Asp Gly Ser Gln Ile Val Thr Ile Leu Ser Asn Lys Gly Ala Ser
            420                 425                 430

Gly Asp Ser Tyr Thr Leu Ser Leu Ser Gly Ala Gly Tyr Thr Ala Gly
        435                 440                 445

Gln Gln Leu Thr Glu Val Ile Gly Cys Thr Thr Val Thr Val Gly Ser
    450                 455                 460

Asp Gly Asn Val Pro Val Pro Met Ala Gly Gly Leu Pro Arg Val Leu
465                 470                 475                 480

Tyr Pro Thr Glu Lys Leu Ala Gly Ser Lys Ile Cys Ser Ser Ser
                485                 490                 495
```

THERMOSTABLE ALPHA AMYLASE

CROSS REFERENCE TO RELATED APPLICATIONS

This application is a § 371 National State Application of PCT/EP2015/068162, filed Aug. 6, 2015, which claims priority to European Application No. 14180205.8 filed Aug. 7, 2014.

BACKGROUND

Field of the Invention

The present invention relates to alpha amylases and to their application in the food, feed and non-food industry.

Description of Related Art

For many years alpha amylases have been used in the baking industry as processing aids. These enzymes are capable of hydrolysing (1→4)-α-D-glucosidic linkages in polysaccharides containing three or more (1→4)-α-linked D-glucose units. Such linkages are found in starch, the major constituent of most types of flour. Flour quality can vary greatly, depending among other things on the growth conditions; wet conditions can for instance lead to pre-harvest sprouting of the grain, with increased levels of alpha-amylase and protease activity and poor baking performance as a result. Wet conditions may lead to pre-harvest sprouting of the grain, with too high levels of alpha-amylase and protease activity and poor baking performance as a result. Wheat flour normally contains relatively high and consistent amounts of beta-amylase, whereas the alpha amylase levels are generally lower. A certain amount of alpha-amylase activity in the flour is needed for a good baking performance.

One of the main challenges in the baking industry is to ensure a consistent quality of baked goods, regardless of the quality of the flour used. To achieve a consistent baking performance flour quality is being standardized. Flour quality is checked at two distinct points in the process from grain harvest to final baked product: at the mill and by the bread improver/bakery. Whereas at the bread improvers/bakeries a range of enzymes are added to produce high specialty flours aimed at specific applications, the aim of the mill is generally to produce a standard flour that can be traded in the market.

At the mill, flour is evaluated on a number of parameters such as moisture, protein content and ash content. In addition, a standard procedure, the falling number test, is performed to measure the alpha-amylase activity. If too little amylase activity is found, the flour can be "corrected" to meet a standard by adding exogenous alpha-amylase, for example in the form of malt flour or by using a fungal amylase. Malt flour has one clear advantage over fungal amylase: it can be used in the falling number test because it influences the falling number. Fungal amylase is less thermostable than malt flour and quickly becomes inactivated in the falling number test procedure. A disadvantage of currently known fungal amylases is that they are less thermostable than alpha-amylase present in malt flour.

During the falling number test procedure, which is performed at temperatures close to 100 degrees Celsius, currently known fungal amylases get more quickly inactivated than alpha-amylase present in malt flour.

Therefore the presence of fungal amylase is not visible in the falling number test. Since the falling number test is a standard procedure this is seen as a disadvantage in the milling industry.

Alpha amylases are also used in other industrial sectors, such as the beverage industry, the brewing industry, the textile industry, the paper industry, the detergent industry, the pharmaceutical industry and the plastics industry, where amylases are used in the production of maltodextrin, modified starches, or glucose and fructose syrups, in the clarification of beer, for desizing textile, for starch modification for coating papers, for the removal of stains and in the production of starch based bioplastics.

SUMMARY OF THE INVENTION

According to a first aspect, the invention relates to a polypeptides having alpha amylase activity and having an amino acid sequence which shows at least 85% identity to amino acids 18 to 495 of SEQ ID No. 1.

According to another aspect, the invention relates to a polynucleotide sequence encoding a polypeptide according to the invention.

According to another aspect, the invention relates to a composition comprising a polypeptide according to the invention. According to another aspect, the invention relates to a composition comprising a polypeptide according to the invention and a dough ingredient and an additional enzyme.

According to another aspect, the invention relates to a composition comprising a polypeptide according to the invention and a dough ingredient.

According to another aspect, the invention relates to a composition comprising a polypeptide according to the invention and an additional enzyme.

According to another aspect, the invention relates to the use of a polypeptide according to the invention for reducing the stirring number or falling number of flour.

According to another aspect, the invention relates to a method for improving a flour, pre-mix or dough using a polypeptide according to the invention.

According to another aspect, the invention relates to a method for preparing a baked product using a polypeptide according to the invention.

According to another aspect, the invention relates to a baked product obtainable by a method according to the invention.

BRIEF DESCRIPTION OF THE DRAWINGS

FIG. 1. Amino acid sequence comprising the AMY1 polypeptide sequence according to the invention; amino acids 1 to 17 represent the pectin methyl esterase (pmeA) signal sequence used for secretion of the mature AMY1 polypeptide, which polypeptide is represented by amino acids 18-495.

FIG. 2. Nucleotide sequence encoding the amino acid sequence depicted in FIG. 1 and which is codon-optimized for expression in *Aspergillus niger*.

FIG. 3. Amino acid sequence comprising the polypeptide sequence of *A. niger* alpha amylase; amino acids 1 to 17 represent the pectin methyl esterase (pmeA) signal sequence used for secretion of the *A. niger* wild type alpha amylase (ANA), which is represented by amino acids 18-495.

FIG. 4. pGBTOP-16 vector used for cloning of AMY1 encoding nucleotide sequence and expression of AMY1 polypeptide according to the invention in *Aspergillus*.

DETAILED DESCRIPTION OF A PREFERRED EMBODIMENT

Description of Sequence Listings

Figure 5:
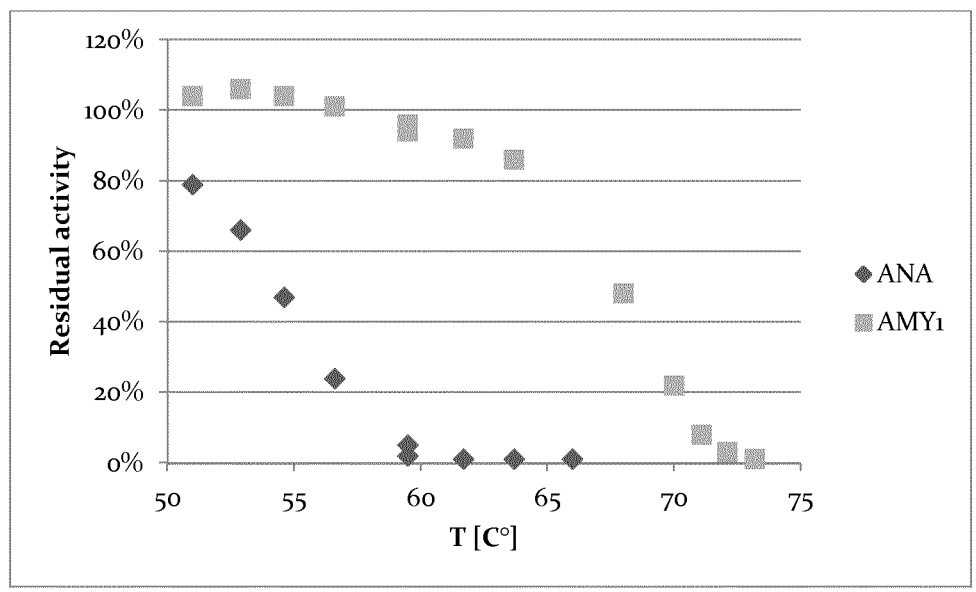
FIG. 5. Residual alpha amylase activity of AMY1 polypeptide according to the invention.

SEQ ID No. 1 sets out the amino acid sequence comprising the AMY1 polypeptide sequence according to the invention, wherein amino acids 1 to 17 represent the pectin methyl esterase (pmeA) signal sequence for secretion of the AMY1 polypeptide and amino acids 18 to 495 represent the secreted AMY1 alpha amylase.

SEQ ID No. 2 sets out the polynucleotide sequence encoding the amino acid sequence of SEQ ID. No. 1, and which is codon-optimized for expression in *Aspergillus niger*.

SEQ ID No. 3 sets out the amino acid sequence comprising the polypeptide sequence of the *A. niger* wild type alpha-amylase polypeptide, wherein amino acids 1 to 17 represent the pectin methyl esterase (pmeA) signal sequence for secretion of the *A. niger* wild type alpha-amylase polypeptide and amino acids 18 to 495 represent the secreted *A. niger* wild type alpha-amylase (ANA).

DETAILED DESCRIPTION OF THE INVENTION

Throughout the present specification and the accompanying claims, the words "comprise", "include" and "having" and variations such as "comprises", "comprising", "includes" and "including" are to be interpreted inclusively. That is, these words are intended to convey the possible inclusion of other elements or integers not specifically recited, where the context allows.

The articles "a" and "an" are used herein to refer to one or to more than one (i.e. to one or at least one) of the grammatical object of the article. By way of example, "an element" may mean one element or more than one element.

The present invention relates to polypeptides which have an amino acid sequence which shows at least 85% identity to amino acids 18 to 495 of SEQ ID No. 1. These novel polypeptides have alpha amylase activity and have an increased thermostability as compared with the alpha-amylase as set out in amino acids 18 to 495 of SEQ ID No. 3. This makes them very suitable for the baking industry where high temperature processes are part of daily practice. For example, polypeptides of the invention may be used for correcting flour and may replace malt flour which is typically used for this purpose. Using the polypeptides according to the invention instead of malt flour has several advantages. Malt flour is less standardized, making consistent results more difficult to obtain. Using the polypeptides of the invention, there is less risk of overdosing and the volumes needed are smaller than when using malt flour, making the handling, storage and transportation easier. In addition, malt flour often contains proteases, which can weaken the dough if added in too high amounts. Another application of the polypeptides of the present invention is in or as a bread or dough improver to improve functionalities of the bread, of the dough or of a baked product made from the dough.

A polypeptide according to the invention has an amino acid sequence which shows at least 85% identity to amino acids 18 to 495 of SEQ ID No. 1. In one embodiment, the polypeptide according to the invention has an amino acid sequence which shows at least 86%, 87%, 88%, 89% or 90% identity to amino acids 18 to 495 of SEQ ID No. 1. In another embodiment, the polypeptide according to the invention has an amino acid sequence which shows at least 91%, 92%, 93%, 94% or 95% identity to amino acids 18 to 495 of SEQ ID No. 1. In another embodiment, the polypeptide according to the invention has an amino acid sequence which shows at least 96%, 97%, 98% or 99% identity to amino acids 18 to 495 of SEQ ID No. 1 or has an amino acid sequence which is identical to amino acids 18 to 495 of SEQ ID No. 1.

In one embodiment of the invention, a polypeptide according to the invention having alpha-amylase activity has an amino acid sequence which has at least 85% identity to amino acids 18 to 495 of SEQ ID No. 1 and which i) when aligned with the alpha-amylase comprising the amino acid sequence as set out in amino acids 18 to 495 of SEQ ID No. 3, comprises at least one substitution of an amino acid residue at one or more positions corresponding to any of positions 22, 46, 48, 50, 52, 64, 65, 80, 84, 89, 91, 94, 109, 111, 126, 143, 155, 158, 161, 166, 168, 170, 171, 173, 174, 177, 194, 196, 197, 198, 199, 201, 203, 208, 209, 210, 238, 245, 249, 262, 263, 277, 280, 286, 287, 301, 303, 310, 323, 326, 331, 332, 335, 338, 346, 353, 364, 370, 372, 381, 382, 384, 388, 394, 396, 397, 402, 406, 408, 409, 422, 423, 425, 429, 434, 443, 450, 454, 455, 456, 463, 465, 474, 483, 484, 487, 490 and 491, wherein said positions are defined with reference to SEQ ID No. 3; or ii) has the amino acid sequence as defined under i) and wherein the polypeptide has an increased thermostability as compared with the alpha-amylase as set out in amino acids 18 to 495 of SEQ ID No. 3; or iii) has the amino acid sequence as defined under i) and wherein the polypeptide reduces the stirring number in a stirring number test as described herein more than the alpha-amylase as set out in amino acids 18 to 495 of SEQ ID No. 3; or iv) has the amino acid sequence as defined under i) and wherein the polypeptide renders improved machinability to a dough in which it is incorporated in comparison to the alpha-amylase as set out in amino acids 18 to 495 of SEQ ID No. 3.

v) has an amino acid sequence as set out in amino acids 18 to 495 of SEQ ID No. 1.

In one embodiment of the invention, a polypeptide according to the invention having alpha-amylase activity has an amino acid sequence which has at least 90% identity to amino acids 18 to 495 of SEQ ID No. 1 and which i) when aligned with the alpha-amylase comprising the amino acid sequence as set out in amino acids 18 to 495 of SEQ ID No. 3, comprises at least one substitution of an amino acid residue at one or more positions corresponding to any of positions 22, 46, 48, 50, 52, 64, 65, 80, 84, 89, 91, 94, 109, 111, 126, 143, 155, 158, 161, 166, 168, 170, 171, 173, 174, 177, 194, 196, 197, 198, 199, 201, 203, 208, 209, 210, 238, 245, 249, 262, 263, 277, 280, 286, 287, 301, 303, 310, 323, 326, 331, 332, 335, 338, 346, 353, 364, 370, 372, 381, 382, 384, 388, 394, 396, 397, 402, 406, 408, 409, 422, 423, 425, 429, 434, 443, 450, 454, 455, 456, 463, 465, 474, 483, 484, 487, 490 and 491, wherein said positions are defined with reference to SEQ ID No. 3; or ii) has the amino acid sequence as defined under i) and wherein the polypeptide has an increased thermostability as compared with the alpha-amylase as set out in amino acids 18 to 495 of SEQ ID No. 3; or iii) has the amino acid sequence as defined under i) and wherein the polypeptide reduces the stirring number in a stirring number test as described herein more than the alpha-amylase as set out in amino acids 18 to 495 of SEQ ID No. 3; or
iv) has the amino acid sequence as defined under i) and wherein the polypeptide renders improved machinability to a dough in which it is incorporated in comparison to the alpha-amylase as set out in amino acids 18 to 495 of SEQ ID No. 3.
v) has an amino acid sequence as set out in amino acids 18 to 495 of SEQ ID No. 1.

In one embodiment of the invention, a polypeptide according to the invention having alpha-amylase activity has an amino acid sequence which has at least 95% identity to amino acids 18 to 495 of SEQ ID No. 1 and which
i) when aligned with the alpha-amylase comprising the amino acid sequence as set out in amino acids 18 to 495 of SEQ ID No. 3, comprises at least one substitution of an amino acid residue at one or more positions corresponding to any of positions 22, 46, 48, 50, 52, 64, 65, 80, 84, 89, 91, 94, 109, 111, 126, 143, 155, 158, 161, 166, 168, 170, 171, 173, 174, 177, 194, 196, 197, 198, 199, 201, 203, 208, 209, 210, 238, 245, 249, 262, 263, 277, 280, 286, 287, 301, 303, 310, 323, 326, 331, 332, 335, 338, 346, 353, 364, 370, 372, 381, 382, 384, 388, 394, 396, 397, 402, 406, 408, 409, 422, 423, 425, 429, 434, 443, 450, 454, 455, 456, 463, 465, 474, 483, 484, 487, 490 and 491, wherein said positions are defined with reference to SEQ ID No. 3; or
ii) has the amino acid sequence as defined under i) and wherein the polypeptide has an increased thermostability as compared with the alpha-amylase as set out in amino acids 18 to 495 of SEQ ID No. 3; or
iii) has the amino acid sequence as defined under i) and wherein the polypeptide reduces the stirring number in a stirring number test as described herein more than the alpha-amylase as set out in amino acids 18 to 495 of SEQ ID No. 3; or
iv) has the amino acid sequence as defined under i) and wherein the polypeptide renders improved machinability to a dough in which it is incorporated in comparison to the alpha-amylase as set out in amino acids 18 to 495 of SEQ ID No. 3.
v) has an amino acid sequence as set out in amino acids 18 to 495 of SEQ ID No. 1.

In one embodiment of the invention, a polypeptide according to the invention having alpha-amylase activity has an amino acid sequence which has at least 85% identity to amino acids 18 to 495 of SEQ ID No. 1 and which
i) when aligned with the alpha-amylase comprising the amino acid sequence as set out in amino acids 18 to 495 of SEQ ID No. 3, comprises at least one substitution of an amino acid residue at one or more positions corresponding to any of positions 22, 46, 48, 50, 52, 64, 65, 80, 84, 89, 91, 94, 109, 111, 126, 143, 155, 158, 161, 166, 168, 170, 171, 173, 174, 177, 194, 196, 197, 198, 199, 201, 203, 208, 209, 210, 238, 245, 249, 262, 263, 277, 280, 286, 287, 301, 303, 310, 323, 326, 331, 332, 335, 338, 346, 353, 364, 370, 372, 381, 382, 384, 388, 394, 396, 397, 402, 406, 408, 409, 422, 423, 425, 429, 434, 443, 450, 454, 455, 456, 463, 465, 474, 483, 484, 487, 490 and 491, wherein said positions are defined with reference to SEQ ID No. 3; or
ii) has the amino acid sequence as defined under i) and wherein the polypeptide has an increased thermostability as compared with the alpha-amylase as set out in amino acids 18 to 495 of SEQ ID No. 3; or
iii) has the amino acid sequence as defined under i) and wherein the polypeptide reduces the stirring number in a stirring number test as described herein more than the alpha-amylase as set out in amino acids 18 to 495 of SEQ ID No. 3; or iv) has the amino acid sequence as defined under i) and wherein the polypeptide renders improved machinability to a dough in which it is incorporated in comparison to the alpha-amylase as set out in amino acids 18 to 495 of SEQ ID No. 3.
v) has an amino acid sequence as set out in amino acids 18 to 495 of SEQ ID No. 1, with the proviso that the variant is not a polypeptide encoded by wildtype DNA.

In one embodiment, of the invention, a polypeptide according to the invention having alpha-amylase activity and having at least 85% identity to the amino acids 18 to 495 of SEQ ID No. 1 has an amino acid sequence which, when aligned with the alpha-amylase comprising the amino acid sequence as set out in amino acids 18 to 495 of SEQ ID No. 3, comprises at least one of the following substitutions:
D22E, T46A, N48D, A50S, Q52R, D64N, K65H, T80S, A84E, T89D, A91G, D94E, E109S, Y111F, E126A, D143A, K155N, S158N, D161S, F166Y, F168L, Q170T, N171D, E173N, D174N, Q177N, D194R, T196E, K197D, D198S, V199D, K201Q, E203I, V208I, G209K, S210E, K238D, I245V, L249F, V262Y, M263L, N277R, K280Q, M286I, D287S, P301A, S303P, V310I, N323S, A326S, V331A, A332I, I335T, N338S, A346Y, A353S, T364L, P370S, D372T, S381T, A382L, A384K, Y388H, T394S, F396Y, V397L, W402Y, K406Q, D408S, T409N, I422V, V423I, I425V, K429L, D434S, A443T, Q450K, V454I, I455Y, G456T, G463D, D465S, G474S, T483A, E484S, A487S, K490G, I491L, wherein the positions are defined with reference to SEQ ID No. 3.

In one embodiment, of the invention, a polypeptide according to the invention having alpha-amylase activity and having at least 90% identity to the amino acids 18 to 495 of SEQ ID No. 1 has an amino acid sequence which, when aligned with the alpha-amylase comprising the amino acid sequence as set out in amino acids 18 to 495 of SEQ ID No. 3, comprises at least one of the following substitutions:
D22E, T46A, N48D, A50S, Q52R, D64N, K65H, T80S, A84E, T89D, A91G, D94E, E109S, Y111F, E126A, D143A, K155N, S158N, D161S, F166Y, F168L, Q170T, N171D, E173N, D174N, Q177N, D194R, T196E, K197D, D198S, V199D, K201Q, E203I, V208I, G209K, S210E, K238D, I245V, L249F, V262Y, M263L, N277R, K280Q, M286I, D287S, P301A, S303P, V310I, N323S, A326S, V331A, A332I, I335T, N338S, A346Y, A353S, T364L, P370S, D372T, S381T, A382L, A384K, Y388H, T394S, F396Y, V397L, W402Y, K406Q, D408S, T409N, I422V, V423I, I425V, K429L, D434S, A443T, Q450K, V454I, I455Y, G456T, G463D, D465S, G474S, T483A, E484S, A487S, K490G, I491L, wherein the positions are defined with reference to SEQ ID No. 3.

In one embodiment, of the invention, a polypeptide according to the invention having alpha-amylase activity and having at least 95% identity to the amino acids 18 to 495 of SEQ ID No. 1 has an amino acid sequence which, when aligned with the alpha-amylase comprising the amino acid sequence as set out in amino acids 18 to 495 of SEQ ID No. 3, comprises at least one of the following substitutions:
D22E, T46A, N48D, A50S, Q52R, D64N, K65H, T80S, A84E, T89D, A91G, D94E, E109S, Y111F, E126A, D143A, K155N, S158N, D161S, F166Y, F168L, Q170T, N171D, E173N, D174N, Q177N, D194R, T196E, K197D, D198S, V199D, K201Q, E203I, V208I, G209K, S210E, K238D, I245V, L249F, V262Y, M263L, N277R, K280Q, M286I, D287S, P301A, S303P, V310I, N323S, A326S, V331A, A332I, I335T, N338S, A346Y, A353S, T364L, P370S, D372T, S381T, A382L, A384K, Y388H, T394S, F396Y, V397L, W402Y, K406Q, D408S, T409N, I422V, V423I, I425V, K429L, D434S, A443T, Q450K, V454I, I455Y, G456T, G463D, D465S, G474S, T483A, E484S, A487S, K490G, I491L, wherein the positions are defined with reference to SEQ ID No. 3.

Optionally, a polypeptide according to the invention having alpha-amylase activity is not a naturally-occurring polypeptide.

The polypeptide of the invention may comprise a substitution at one or more of the said positions, for example at two, three, four, at least 5, at least 10, at least 15, at least 20, at least 25, at least 30, at least 35, at least 40, at least 45, at least 50, at least 55, at least 60, at least 65, at least 70 or at all of the said positions.

Polypeptides of the invention may vary in length among each other, as long as they show at least 85% identity to amino acids 18 to 495 of SEQ ID No. 1, have alpha amylase activity and have an increased thermostability as compared with the alpha-amylase as set out in amino acids 18 to 495 of SEQ ID No. 3. Such variations in length may have been made on purpose or may have been unintended. For example, upon maturation and secretion some raffling of N- and C-termini may occur, which might result in a slightly extended mature polypeptide or a slightly truncated mature polypeptide. The mature polypeptide of sequence SEQ ID No. 1 having alpha amylase activity may comprise amino acids 13, 14, 15, 16, 17, 18, 19, 20, 21, 22, 23, or 24 to amino acid 485, 486, 487, 488, 489, 490, 491, 492, 493 or 495 of SEQ ID No. 1, wherein the methionine at position 1 in SEQ ID No. 1 is counted as number 1. Advantageously, the mature polypeptide sequence having alpha amylase activity comprises amino acids 18 to 495 of SEQ ID No. 1.

In the context of the present invention, in order to determine the percentage of sequence identity of two amino acid sequences or of two nucleic acid sequences, the sequences are aligned for optimal comparison purposes. In order to optimize the alignment between the two sequences, gaps may be introduced in any of the two sequences that are compared. Such alignment may be carried out over the full length of the sequences being compared. Alternatively, the alignment may be carried out over a shorter length, for example over about 20, about 50, about 100 or more nucleic acids/bases or amino acids. The sequence identity is the percentage of identical matches between the two sequences over the reported aligned region. Upon the alignment of two sequences the resulting aligned amino acid positions are usually referred to as corresponding positions. The percent sequence identity between two amino acid sequences or between two nucleotide sequences may be determined using the Needleman and Wunsch algorithm for the alignment of two sequences. (Needleman, S. B. and Wunsch, C. D. (1970) J. Mol. Biol. 48, 443-453). Both amino acid sequences and nucleotide sequences can be aligned by the algorithm. The Needleman-Wunsch algorithm has been implemented in the computer program NEEDLE. For the purpose of this invention the NEEDLE program from the EMBOSS package was used (version 2.8.0 or higher, EMBOSS: The European Molecular Biology Open Software Suite (2000) Rice,P. Longden,l. and Bleasby,A. Trends in Genetics 16, (6) p. 276-277, at emboss.bioinformatics.nl). For protein sequences EBLOSUM62 is used for the substitution matrix. For nucleotide sequences, EDNAFULL is used. The optional parameters used are a gap-open penalty of 10 and a gap extension penalty of 0.5. The skilled person will appreciate that all these different parameters will yield slightly different results but that the overall percentage identity of two sequences is not significantly altered when using different algorithms.

After alignment by the program NEEDLE as described above the percentage of sequence identity between a query sequence and a sequence of the invention is calculated as follows: Number of corresponding positions in the alignment showing an identical amino acid or identical nucleotide in both sequences divided by the total length of the alignment after subtraction of the total number of gaps in the alignment. The identity as defined herein can be obtained from NEEDLE by using the NOBRIEF option and is labeled in the output of the program as "longest-identity".

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) J. Mol. Biol. 215:403-10. BLAST nucleotide searches can be performed with the NBLAST program, score=100, word length=12 to obtain nucleotide sequences similar to nucleic acid molecules of the invention. BLAST protein searches can be performed with the XBLAST program, score=50, word length=3 to obtain amino acid sequences similar to protein molecules of the invention. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., XBLAST and NBLAST) can be used. See the homepage of the National Center for Biotechnology Information at www.ncbi.nlm.nih.gov.

The polypeptides according to the invention may be obtained by any suitable means. In one embodiment, they are isolated from a source, in particular a prokaryotic or eukaryotic microorganism, containing the polypeptide. Suitable examples of microorganisms are mammalian, plant, fungal and algal microorganisms as mentioned below. In one embodiment, a polypeptide according to the invention is isolated from a thermophilic fungus. In another embodiment, the polypeptides according to the invention, are generated using standard molecular biology techniques e.g. by de novo synthesis. In another embodiment, polypeptides according to the invention are generated starting from an existing amino acid sequence, for example of an amino acid sequence coding for an alpha amylase, using site-saturation mutagenesis, scanning mutagenesis, insertional mutagenesis, random mutagenesis, site-directed mutagenesis, and directed-evolution, as well as various other recombination approaches known to a skilled person in the art.

A polypeptide according to the present invention may be a fusion protein. Techniques for producing fusion polypeptides are known in the art, and include ligating the coding sequences encoding the polypeptides so that they are in frame. Expression of the fused polypeptide is under control of the same promoter (s) and terminator. The hybrid polypeptides may comprise a combination of partial or complete polypeptide sequences obtained from at least two different polypeptides wherein one or more may be heterologous to a host cell. Such fusion polypeptides from at least two different polypeptides may comprise a binding domain from one polypeptide, such as a starch binding domain or a carbohydrate binding domain, operably linked to a catalytic domain from a second polypeptide. Examples of fusion polypeptides and signal sequence fusions are for example as described in WO2010/121933, WO2013/007820 and WO2013/007821.

In the context of the present invention the term 'polypeptide' refers to a molecule which contains a backbone of a chain of at least ten amino acids, wherein the amino acids are covalently linked to each other by peptide bonds. These backbone amino acids groups may be linked to other groups, such as other amino acid sequences, sugar groups or lipid groups. The polypeptide may contain structural features, such as alpha-helices, beta-pleated sheets or disulphide bridges. A polypeptide according to the present invention may comprise a catalytic domain and one or more binding domains, such as a starch or carbohydrate binding domain. In the context of the present invention, the amino acid sequence is also referred to as 'polypeptide sequence' or 'protein sequence'. The term 'polypeptides' includes proteins.

In one embodiment, the polypeptides according to the invention comprise only conventional or natural amino acids, for example such as mentioned in FIG. 1 and FIG. 2, which depict the sequences of two polypeptides of the invention. In the Figures and in other places of the description of the present invention, the one letter code for amino acids is used, where A stands for Alanine, I for Isoleucine, L for Leucine, V for Valine, S for Serine, G for Glycine, P for Proline, Q for Glutamine, E for Glutamic acid, R for Arginine, D for Aspartic acid, K for Lysine, N for Asparagine, Y for Tyrosine, H for Histidine, F for Phenylalanine, C for Cysteine, T for Threonine. In the one letter code for amino acids M stands for Methionine, W for Tryptophan.

Such one letter codes are commonly known in the art, see e.g. Sambrook, et al. (Molecular Cloning: A Laboratory Manual, $2^{nd}$ ed. Cold Spring Harbor Laboratory, Cold Spring Harbor Laboratory Press, Cold Spring Harbor, N.Y., 1989).

In another embodiment, the polypeptide according to the invention also or exclusively comprises unnatural amino acids, for example such as available from Sigma Aldrich, Co.

Polypeptides according to the invention have alpha amylase activity. Alpha amylase activity is defined as endohydrolysis of (1→4)-α-D-glucosidic linkages in polysaccharides containing three or more (1→4)-α-linked D-glucose units. Alpha amylases (1,4 alpha glucan-4-glucanohydrolases, EC 3.2.1.1) are also referred to as glycogenases, endoamylases or 1,4-α-D-glucan glucanohydrolases.

Alpha amylase activity is preferably determined using the alpha amylase assay as described herein. Thermostability may be determined by measuring the Residual Activity as described herein. Residual Activity is defined as the ratio of the alpha amylase activity at 37 degrees C. after incubation at elevated temperature to the alpha amylase activity at 37 degrees C. without a heating step, i.e. without such incubation at elevated temperature. A polypeptide having alpha amylase activity has an increased thermostability if its Residual Activity is higher compared to the Residual Activity of the alpha-amylase as set out in amino acids 18 to 495 of SEQ ID No. 3.

Alpha amylase activity may suitably be determined at 37 degrees C. and pH 5.2, unless otherwise indicated, using a non-reducing-end blocked p-nitrophenyl maltoheptaoside substrate (=BPNPG7) combined with excess levels of thermostable α-glucosidase and amyloglucosidase (Megazyme Ceralpha kit). Hydrolysis of BPNPG7 substrate by endo-acting α-amylase activity results in p-nitrophenyl maltosaccharide fragments. Excess quantities of α-glucosidase present in the reaction mixture result in instantaneous and quantitative hydrolysis of this p-nitrophenyl maltosaccharide fragment resulting into glucose and free p-nitrophenol. The reaction is terminated (and colour developed) by the addition of an alkaline solution. The absorbance at a wavelength of 405 nm is determined and is a measure for enzymatic activity.

In one embodiment, alpha amylase activity is calculated from a molar extinction coefficient determination through a calibration with a para-nitrophenol solution of known concentration. Sample dilutions are prepared in 50 mM malic acid buffer pH 5.2, containing 50 mM NaCl, 2 mM CaCl2 and 0.05% BSA, for example in a range of 0.03 to 0.15 U/ml. Ceralpha assay reagent (R-CAAR-4) from a Megazyme α-amylase kit test (Ceralpha, R-CAAR-4) is dissolved in 10 ml water, to which 8 ml of the malic acid buffer is added. After preheating 540 μl of this substrate in 2 ml eppendorf vials in a water bath at the indicated temperatures, 60 μl of sample dilution is added to start the incubation. The reaction is terminated after 7 minutes and 5 seconds by addition of 450 μl of a 170 mM Tris solution. Samples are stored on ice until the absorbance at 405 nm is recorded. Sample blanks are measured by reversing the pipetting order: first stop reagent, then sample and substrate. Alpha amylase activity is calculated from the delta absorbance between sample and blank incubations using the para-nitrophenol molar extinction coefficient determined in the same series according to:

$$U/g \text{ sample} = [1000 \times (Abs_{sample} - Abs_{blank})/(\varepsilon pNP \times 7.05) \times 175/10 \times Df)]/W$$

where:
1000=factor from mmol to μmol
$Abs_{sample} - Abs_{blank}$=absorbance in sample incubation corrected for absorbance in blank incubation
εpNP=Molar Extinction Coefficient of para-nitro-phenol [L·mol-1·cm-1]
7.05=Incubation time [min]
175=assay final volume [μL]
10=sample volume [μL]
Df=Dilution factor
W=sample weight [g]
U=μmol/min In one embodiment, the alpha amylase activity is the only enzyme activity of the polypeptide according to the invention. In another embodiment, the alpha amylase activity is the main enzyme activity of the polypeptide according to the invention.

Polypeptides of the invention have a low Act25/Act37 ratio of $$\frac{\text{alpha amylase activity at 25 degrees C.}}{\text{alpha amylase activity at 37 degrees C.}} \times 100\%$$

and/or have a low $Act30/Act37$ ratio of $$\frac{\text{alpha amylase activity at 30 degrees C.}}{\text{alpha amylase activity at 37 degrees C.}} \times 100\%,$$

wherein the alpha amylase activity is preferably measured as described herein.

The Act25/Act37 ratio is defined as:

$$\frac{\text{alpha amylase activity at 25 degrees C.}}{\text{alpha amylase activity at 37 degrees C.}} \times 100\%,$$

wherein the alpha amylase activity is preferably measured as described herein.

The said Act25/Act37 ratio is defined as:

$$\frac{\text{alpha amylase activity at 30 degrees C.}}{\text{alpha amylase activity at 37 degrees C.}} \times 100\%,$$

wherein the alpha amylase activity is preferably measured as described herein.

The Act25/Act37 ratio and Act 30/37 ratio are also referred to herein as Relative Activity. In one embodiment, this ratio is lower than 70% at 30 degrees C. and lower than 50% at 25 degrees C. In another embodiment, this ratio is between 50% and 65% at 30 degrees C. and between 30% and 45% at 25 degrees C. In another embodiment, this ratio is about 60% at 30 degrees C. and about 40% at 25 degrees C. for a polypeptide according to the invention.

In one embodiment the polypeptide of the invention has an Act30/Act37 ratio lower than 70% or an Act 25/37 ratio lower than 50%.

In one embodiment the polypeptide of the invention has an Act30/Act37 ratio lower than 70% and an Act 25/37 ratio lower than 50%.

In another embodiment, the polypeptide of the invention has an Act30/Act37 ratio of 50% to 65% and an Act25/Act37 ratio of 30% to 45%.

In another embodiment, the polypeptide of the invention has an Act30/Act37 ratio of about 60% and an Act25/Act37 ratio of about 40%.

Polypeptides according to the invention are thermostable, which is indicated by high residual alpha amylase activity at elevated temperature. Residual alpha amylase activity (referred to as Residual Activity) is defined as the ratio of the activity at 37 degrees C. after incubation at elevated temperature to the activity at 37 degrees C. without a heating step.

Residual Activity =

$$\frac{\text{Activity at 37 degrees C. after 15 min elevated } T}{\text{Activity at 37 degrees C. without elevated } T} \times 100\%$$

Polypeptides according to the invention have increased thermostability as compared with the alpha-amylase as set out in amino acids 18 to 495 of SEQ ID No. 3. In one embodiment, polypeptides according to the invention have at least 80%, at least 85%, at least 86%, at least 87%, at least 88%, at least 89% or at least 90% residual alpha amylase activity after 15 minutes at pH 5.2 at a temperature in the range of 51 to 61 degrees C.

In another embodiment, polypeptides according to the invention have
at least 90%, at least 95% or at least 100% residual alpha amylase activity after 15 minutes at 51 degrees C. at pH 5.2, or
at least 80%, at least 85%, at least 90%, at least 95% or at least 100% residual alpha amylase activity after 15 minutes at 55 degrees C. at pH 5.2 or
at least 80%, at least 85% or at least 90% residual alpha amylase activity after 15 minutes at 60 degrees C. at pH 5.2, or
at least 15%, at least 18% or at least 20% residual alpha amylase activity after 15 minutes at 70 degrees C. at pH 5.2.

In one embodiment, a polypeptide according to the invention has at least 90%, at least 95% or at least 100% residual alpha amylase activity after 15 minutes at 51 degrees C. at pH 5.2 and at least 15%, at least 18% or at least 20% residual alpha amylase activity after 15 minutes at 70 degrees C. at pH 5.2.

In one embodiment, a polypeptide according to the invention has at least 80%, at least 85%, at least 90%, at least 95% or at least 100% residual alpha amylase activity after 15 minutes at 55 degrees C. at pH 5.2 and at least 80%, at least 85% or at least 90%, residual alpha amylase activity after 15 minutes at 60 degrees C. at pH 5.2.

In another embodiment, a polypeptide according to the invention has at least 80%, at least 85%, at least 90%, at least 95% or at least 100% residual alpha amylase activity after 15 minutes at 55 degrees C. at pH 5.2 and at least 20%, at least 25% at least 30%, at least 35%, at least 40%, at least 45% residual alpha amylase activity after 15 minutes at 68 degrees C. at pH 5.2.

In another embodiment, a polypeptide according to the invention has at least 80%, at least 85%, at least 90%, at least 95% or at least 100% residual alpha amylase activity after 15 minutes at 55 degrees C. at pH 5.2 and at least 15%, at least 18% or at least 20% residual alpha amylase activity after 15 minutes at 70 degrees C. at pH 5.2, In yet another embodiment, a polypeptide according to the invention has at least 80%, at least 85% or at least 90% residual alpha amylase activity after 15 minutes at 60 degrees C. at pH 5.2 and at least 20%, at least 25% at least 30%, at least 35%, at least 40%, at least 45% residual alpha amylase activity after 15 minutes at 68 degrees C. at pH 5.2, In another embodiment, a polypeptide according to the invention has at least 80%, at least 85% or at least 90% residual alpha amylase activity after 15 minutes at 60 degrees C. at pH 5.2 and at least 15%, at least 18% or at least 20% residual alpha amylase activity after 15 minutes at 70 degrees C. at pH 5.2, In yet another embodiment, a polypeptide according to the invention has at least 90%, at least 95% or at least 100% residual alpha amylase activity after 15 minutes at 51 degrees C. at pH 5.2, at least 80%, at least 85%, at least 90%, at least 95% or at least 100% residual alpha amylase activity after 15 minutes at 55 degrees C. at pH 5.2, at least 80%, at least 85% or at least 90% residual alpha amylase activity after 15 minutes at 60 degrees C. at pH 5.2, at least 20%, at least 25% at least 30%, at least 35%, at least 40%, at least 45% residual alpha amylase activity after 15 minutes at 68 degrees C. at pH 5.2 and at least 15%, at least 18% or at least 20% residual alpha amylase activity after 15 minutes at 70 degrees C. at pH 5.2, Polypeptides according to the invention have their pH optimum at a pH in the range of 4 to 7.

In another aspect, the present invention relates to a nucleotide sequence encoding a polypeptide according to the invention. In the context of the present invention, the term nucleotide sequence refers to a chain of nucleotides in a specific order and this sequence may also be referred to as a polynucleotide sequence or a nucleic acid sequence. In another aspect, the present invention relates to a polynucleotide sequence comprising a polynucleotide sequence encoding a polypeptide according to the invention. A nucleotide sequence according to the present invention may be generated using standard molecular biology techniques well known to those skilled in the art. For example, using standard synthetic techniques, the required nucleotide sequence may be synthesized de novo, typically by an automated process. Alternatively, a nucleotide sequence of the invention may be generated using site-directed mutagenesis of an existing nucleotide sequence, for example a naturally occurring nucleotide sequence coding for an alpha amylase. Site-directed mutagenesis may be carried out using a number of techniques well know to those skilled in the art. Yet alternatively, the nucleotide sequence of the invention may be obtained by isolation from a cell, in particular from a prokaryotic or eukaryotic cell. Suitable examples of such cells are mammalian, plant, fungal and algal cells from organisms mentioned below. The nucleotide sequence is typically DNA, such as genomic DNA, cDNA or synthetic DNA; or RNA, such as mRNA, and may be double stranded or single stranded. A nucleotide sequence according to the invention is depicted in FIG. 2 and in SEQ ID No. 2. After production, such as by synthesis, generation by mutagenesis or isolation from an organism, the nucleotide sequence of the invention may be partially or completely purified.

In another aspect, the present invention relates to a nucleic acid molecule, comprising the afore-mentioned nucleotide sequence encoding a polypeptide according to the invention. In another aspect, the present invention relates to a nucleic acid molecule, comprising the polynucleotide sequence encoding the polypeptide according to the invention. The nucleic acid molecule may be generated using standard molecular biology techniques well known to those skilled in the art and e.g. may be generated de novo using standard synthetic techniques or by recombinant technology. The nucleic acid molecule may be DNA or RNA, double stranded or single stranded. The nucleic acid molecule encoding a polypeptide according to the invention may comprise a sequence which is optimized for expression in a prokaryotic or eukaryotic, in particular, mammalian, plant or fungal, host cell. The nucleic acid molecule encoding a polypeptide according to the invention will typically contain a promoter sequence and a terminator sequence. It may contain other expression regulating elements, including a signal sequence, selection markers, enhancers, silencers and insulators. The nucleic acid molecule according to the invention may be or be part of a vector. In one embodiment, the vector is an expression vector, wherein the nucleotide sequence according to the invention is operably linked with at least one regulatory sequence allowing for expression of the nucleotide sequence in a suitable host cell. The vector may contain certain restriction sites which may be unique to the vector.

In yet another aspect, the present invention relates to a recombinant host cell comprising a nucleotide sequence or a nucleic acid molecule according to the invention, in particular to a microorganism transformed with a nucleotide sequence or nucleic acid molecule, such as a vector, encoding a polypeptide according to the invention. This microorganism may be any microorganism which can produce polypeptide of the invention, optionally after special technical measures, such as optimization of the nucleotide sequence. In one embodiment, the microorganism transformed with a nucleotide sequence or nucleic acid molecule encoding a polypeptide according to the invention is a prokaryotic cell, such as a Gram-negative or Gram-positive bacterium. Suitable bacteria include *Escherichia, Anabaena, Caulobactert, Cyanobacteria, Gluconobacter, Rhodobacter, Pseudomonas, Paracoccus, Bacillus, Brevibacterium, Corynebacterium, Rhizobium (Sinorhizobium), Flavobacterium, Klebsiella, Enterobacter, Lactobacillus, Lactococcus, Methylobacterium, Moraxella, Neisseria, Staphylococcus, Streptomyces* or *Thermoactinomyces*. In another embodiment, the microorganism is a eukaryotic cell, such as a mammalian cell, insect cell, plant cell, fungal cell or algal cell. Suitable examples of mammalian cells are CHO cells, COS cells, 293 cells, Per.C6® cells, and hybridomas. Suitable examples of insect cells include Sf9 and Sf21 cells and derivatives thereof. Suitable examples of fungal cells include yeast cells, such as *Candida, Hansenula, Kluyveromyces, Pichia, Saccharomyces, Schizosaccharomyces*, or *Yarrowia* strain; more preferably *Kluyveromyces lactis, S. cerevisiae, Hansenula polymorpha, Yarrowia lipolytica* and *Pichia pastoris*, or a filamentous fungi. Filamentous fungi include all filamentous forms of the subdivision Eumycota and Oomycota (as defined by Hawksworth et al., In, Ainsworth and Bisby's Dictionary of The Fungi, 8th edition, 1995, CAB International, University Press, Cambridge, UK). Filamentous fungal strains include strains of *Acremonium, Agaricus, Aspergillus, Aureobasidium, Chrysosporium, Coprinus, Cryptococcus, Filibasidium, Fusarium, Humicola, Magnaporthe, Mucor, Myceliophthora, Neocallimastix, Neurospora, Paecilomyces, Penicillium, Piromyces, Panerochaete, Pleurotus, Rasamsonia, Schizophyllum, Talaromyces, Thermoascus, Thielavia, Tolypocladium*, and *Trichoderma*. Preferred filamentous fungal cells belong to a species of an *Aspergillus, Chrysosporium, Myceliophthora, Penicillium, Talaromyces, Fusarium, Rasamsonia, Thermoascus* or *Trichoderma* genus, and most preferably a species of *Aspergillus niger, Aspergillus awamori, Aspergillus foetidus, Aspergillus sojae, Aspergillus fumigatus, Aspergillus oryzae, Fusarium oxysporum, Myceliophthora thermophila, Rasamsonia emersonii, Trichoderma reesei, Talaromyces emersonii, Thermoascus aurantiacus* or *Penicillium chrysogenum*. Algae is the group of unicellular and multicellular eukaryortic photosynthetic organisms, including microalgae, such as *Dunaliella, Spirulina* and *Chlorella*. In one embodiment, the recombinant host cell comprising a nucleotide sequence or a nucleic acid molecule according to the invention is an *Aspergillus, Bacillus, Chrysosporium, Escherichia, Kluyveromyces, Myceliophthora, Penicillium, Pseudomonas, Rasamsonia, Saccharomyces, Streptomyces* or *Talaromyces* species, preferably a *Bacillus subtilis, Bacillus amyloliquefaciens, Bacillus licheniformis, Escherichia coli, Aspergillus niger, Aspergillus oryzae, Myceliophthora thermophila, Rasamsonia emersonii* or *Trichoderma reesei* species. The recombinant host cell is preferably capable of expressing or overexpressing the nucleotide sequence or nucleic acid molecule according to the invention. The recombinant microbial host cell may further comprise one or more modifications in its genome such that the recombinant microbial host cell is deficient in the production of at least one product selected from glucoamylase (glaA), acid stable alpha-amylase (amyA), neutral alpha-amylase (amyBI and amyBII), oxalic acid hydrolase (oahA), a toxin, preferably ochratoxin and/or fumonisin, a protease transcriptional regulator prtT, PepA, a product encoded by the gene hdfA and/or hdfB, a non-ribosomal peptide synthase npsE, agsE or amyC if compared to a parent host cell and measured under the same conditions. Suitable methods of producing said host cells include the ones described in WO2011/009700, WO2012/001169, WO2014013074.

A method for preparing a nucleotide sequence according to the invention or a nucleic acid molecule according to the invention, comprising the steps of culturing a host cell transformed with a nucleotide sequence or a nucleic acid molecule according to the invention and isolating said nucleotide sequence or nucleic acid molecule, such as a vector, from the host cell is also encompassed by the present invention.

There are several ways of inserting a nucleic acid into a nucleic acid construct or an expression vector which are known to a skilled person in the art. It may be desirable to manipulate a nucleic acid encoding a polypeptide of the present invention with control sequences, such as promoter and terminator sequences. Any promoter sequence suitable for a eukaryotic or prokaryotic host cell, which shows transcriptional activity, including mutant, truncated, and hybrid promoters, may be used and may be obtained from polynucleotides encoding extracellular or intracellular polypeptides either endogenous (native) or heterologous (foreign) to the cell. The promoter may be a constitutive or inducible promoter. Preferably, the promoter is an inducible promoter, for instance a starch inducible promoter. Promoters suitable in filamentous fungi are promoters which may be selected from the group, which includes but is not limited to promoters obtained from the polynucleotides encoding *A. oryzae* TAKA amylase, *Rhizomucor miehei* aspartic proteinase, *Aspergillus* gpdA promoter, *A. niger* neutral alpha-amylase, *A. niger* acid stable alpha-amylase, *A. niger* or *A. awamori* glucoamylase (glaA), *A. niger* or *A. awamori* endoxylanase (xlnA) or beta-xylosidase (xlnD), *T. reesei* cellobiohydrolase I (CBHI), *R. miehei* lipase, *A. oryzae* alkaline protease, *A. oryzae* triose phosphate isomerase, *A. nidulans* acetamidase, *Fusarium venenatum* amyloglucosidase (WO 00/56900), *Fusarium venenatum* Dania (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the polynucleotides encoding *A. niger* neutral alpha-amylase and *A. oryzae* triose phosphate isomerase), and mutant, truncated, and hybrid promoters thereof. Other examples of promoters are the promoters described in WO2006/092396 and WO2005/100573, which are herein incorporated by reference. Suitable promoters in eukaryotic host cells may be GAL7, GAL10, or GAL1, CYC1, HIS3, ADH1, PGL, PH05, GAPDH, ADC1, TRP1, URA3, LEU2, ENO1, TPI1, and AOX1. Other suitable promoters include PDC1, GPD1, PGK1, TEF1, and TDH3. All of the above-mentioned promoters are readily available in the art.

Suitable inducible promoters useful in bacteria, such as Bacilli, include: promoters from Gram-positive microorganisms such as SP01-26, SP01-15, veg, pyc (pyruvate carboxylase promoter), and amyE. Examples of promoters from Gram-negative microorganisms include, but are not limited to, tac, tet, trp-tet, lpp, lac, lpp-lac, lacIq, T7, T5, T3, gal, trc, ara, SP6, λ-PR, and λ-PL.

Any terminator which is functional in a cell as disclosed herein may be used. Such terminators are known in the art and include terminator sequences of filamentous fungal genes, such as from *Aspergillus* genes, for instance from the gene *A. oryzae* TAKA amylase, the genes encoding *A. niger* glucoamylase (glaA), *A. nidulans* anthranilate synthase, *A. niger* alpha-glucosidase, trpC and/or *Fusarium oxysporum* trypsin-like protease A method for preparing the polypeptide according to the invention comprising cultivating a recombinant host cell according to the invention under conditions which allow for expression of the polynucleotide sequence according to the invention or the nucleic acid molecule according to the invention and, optionally, recovering the encoded polypeptide from the cell or culture medium is also encompassed by the present invention.

Polypeptides according to the invention may be isolated or partially or completely purified from the environment in which they were produced, typically a culture broth, by conventional means, including centrifugation, filtration, such as ultrafiltration and bottle-top filtration, extraction, precipitation, evaporation and spray-drying. They may be further purified by methods known in the art, such as chromatography, extraction or electrophoretic procedures. In one embodiment, a polypeptide of the invention is used after separation of the culture broth from the biomass without further purification steps.

Polypeptides according to the invention may be formulated. Suitable formulations include liquid formulations, such as emulsions, suspensions and solutions; pastes, gels, granules and freeze-dried or spray-dried powders.

In yet another aspect, the present invention relates to a composition consisting of or comprising a polypeptide according to the invention.

According to another aspect, the invention relates to a composition comprising a polypeptide according to the invention and a dough ingredient and an additional enzyme.

According to another aspect, the invention relates to a composition comprising a polypeptide according to the invention and a dough ingredient.

According to another aspect, the invention relates to a composition comprising a polypeptide according to the invention and an additional enzyme.

The amount of the polypeptide according to the invention in the composition according to the invention may be between 0.001% and 100% w/w the based on total protein. Preferably, the composition comprises between 1% and 70% w/w of the polypeptide based on total protein. In one embodiment, the preparation comprises between 1% and 50% w/w of the polypeptide according to the invention based on total protein. In yet another embodiment, the preparation comprises between 1% and 30% w/w of the polypeptide according to the invention based on total protein. In yet another embodiment, the preparation comprises between 5% and 20% w/w of the polypeptide according to the invention based on total protein. In one embodiment of the invention, the polypeptide according to the invention is the only enzymatic component in the preparation.

In another embodiment of the invention, the composition comprises a polypeptide of the invention and at least one additional enzymatic activity. The at least one additional enzyme activity may be selected from enzymes like a protease, such as a endoprotease or an exoprotease; a peptidase, such as an exopeptidase or an endopeptidase; a lipolytic enzyme, such as a triacyl glycerol lipase, a phospholipase, a galactolipase or an enzyme having both phospholipase and galactolipase activity; or a carbohydrase, such as a cellulase, a hemicellulase, in particular a pentosanase such as a xylanase; a cross-linking enzyme, such as a transglutaminase; a maltogenic alpha amylase; a further amylase such as a further alpha amylase or a beta amylase; an oxidase, a peroxidase, a hexose oxidase, a laccase; a protein disulfide isomerase; an asparaginase.

In one embodiment, the invention relates to a composition comprising the polypeptide according to the invention and one or more selected from the group consisting of milk powder, gluten, granulated fat, an additional enzyme, an amino acid, a salt, an oxidant such as ascorbic acid, bromate and azodicarbonamide, a reducing agent such as L-cysteine, an emulsifier such as mono-glycerides, di-glycerides, glycerol monostearate, sodium stearoyl lactylate, calcium stearoyl lactylate, polyglycerol esters of fatty acids and diacetyl tartaric acid esters of mono- and diglycerides, gums such as guargum and xanthangum, flavours, acids such as citric acid and propionic acid, starch, modified starch, gluten, humectants such as glycerol, and preservatives.

In one embodiment, the invention relates to a composition comprising the polypeptide according to the invention and one or more components selected from the group consisting of milk powder, gluten, granulated fat, an additional enzyme, an amino acid, a salt, an oxidant such as ascorbic acid, bromate and azodicarbonamide, a reducing agent such as L-cysteine, an emulsifier such as mono-glycerides, diglycerides, glycerol monostearate, sodium stearoyl lactylate, calcium stearoyl lactylate, polyglycerol esters of fatty acids and diacetyl tartaric acid esters of mono- and diglycerides, gums such as guargum and xanthangum, flavours, acids such as citric acid and propionic acid, starch, modified starch, gluten, humectants such as glycerol, and preservatives. The additional enzyme may be selected from enzymes like a protease, such as a endoprotease or an exoprotease; a peptidase, such as an exopeptidase or an endopeptidase; a lipolytic enzyme, such as a triacyl glycerol lipase, a phospholipase, a galactolipase or an enzyme having both phospholipase and galactolipase activity; or a carbohydrase, such as a cellulase, a hemicellulase, in particular a pentosanase such as a xylanase; a cross-linking enzyme, such as a transglutaminase; a maltogenic alpha amylase; a further amylase such as a further alpha amylase or a beta amylase; an oxidase, a peroxidase, an hexose oxidase, a glucose oxidase, a laccase; a protein disulfide isomerase; an asparaginase In one embodiment, the composition further comprises a lipolytic enzyme, preferably a phospholipase. In another embodiment, the composition comprises an alpha amylase according to the invention and an asparaginase. In another embodiment, the composition comprises an alpha amylase according to the invention and a further amylase. In another embodiment, the composition comprises an alpha amylase according to the invention and a maltogenic alpha amylase.

The polypeptide of the invention may be included in a pre-mix. The term "pre-mix" is defined herein to be understood in its conventional meaning, i.e. as a mix of baking agents, generally including flour, which may be used not only in industrial bread-baking plants/facilities, but also in retail bakeries. The pre-mix may be prepared by mixing the polypeptide according to the invention or the enzyme composition according to the invention with a suitable carrier such as flour, starch or a salt. The pre-mix may contain additives as mentioned herein.

The composition according to the invention may be formulated in any suitable form. In one embodiment, the composition according to the invention is formulated in a dry form, such as a freeze-dried or spray-dried powder. In another embodiment, the composition according to the invention is in liquid form, such as in the form of an emulsion, a suspension or a solution. In yet another embodiment, the composition according to the invention is formulated as a gel, granule or paste.

In yet another aspect, the present invention relates to the use of a polypeptide according to the invention or a composition according to the invention in the baking industry. In one embodiment, a polypeptide or a composition according to the invention is used for correcting flour, in particular for influencing the falling number in a falling number test. Especially flour intended for bread production must have sufficient levels of alpha amylase to be able to provide the dough and bread with the required functional properties. The polypeptide according to the invention may be used for alpha amylase supplementation of low alpha amylase flour until the desired alpha amylase content is reached. Alpha amylase content of flour can then be determined by the falling number test, because the polypeptides of the invention are effective in this test. The test, first developed by Sven Hagberg (S. Hagberg (1960) Cereal Chem 37: 218), is based on the fact that alpha-amylases will reduce the viscosity of a starch paste. Suitable falling number tests include the internationally standardized ICC 107/1, ISO 3093-2004, AACC 56-81B methods. To perform a falling number test, flour is mixed with water at a certain ratio and shaken to produce a flour slurry. The sample is inserted in the falling number instrument where it is quickly heated up by a boiling water bath, so that the starch gelatinizes. After an initial waiting time of 5 seconds, followed by stirring for 55 seconds the stirrer is released and allowed to fall through the mixture. The time it takes for the stirrer to reach the bottom of the tube, including the initial 60 seconds wait/stirring, is defined as the falling number. The higher the amylase activity in the flour, the lower the viscosity of the paste and therefore the lower the resulting falling number. The falling number is therefore inversely related to amylase activity, and can be used as an indirect measure of this. Since state of the art fungal amylases are inactivated by the heat step before they can have an effect, malt flour is typically used in the falling number test for flour correction. Using the polypeptides according to the invention, it is now possible to replace the malt flour in the falling number test by an alpha amylase preparation according to the invention. This replacement contributes to the ease of handling and of transportation, because the polypeptides according to the invention may be used in a more concentrated form than malt flour. In addition, the quality of the polypeptides according to the invention is more standardized. Malt flour generally contains proteases and the amylase activity in the malt flour can vary from batch to batch.

The polypeptide according to the invention or a composition according to the invention may also be used in a stirring number test, which is based on the same physical principle as the falling number test. The stirring number test may suitably be performed using a Rapid Visco Analyzer (RVA). As in the falling number test, a flour slurry is prepared, by mixing 3.5 g flour with 25 ml $H_2O$. The sample is placed in the RVA and quickly heated up to 95° C. The sample is stirred in the RVA, while the viscosity is measured. The stirring number is defined as the viscosity measured after 180 seconds.

The stirring number may be determined using the RVA™ stirring number method (RVA 02.04) from Perten.

Alpha-amylase activity decreases the viscosity and leads to a lower stirring number. Samples with little alpha-amylase activity will have a high stirring number and therefore, the falling number and the stirring number of a sample are correlated. Therefore, in one aspect the present invention relates to a method for improving flour quality, which method comprises adding an effective amount of the polypeptide or the composition according to the invention to flour to reduce the falling number. In one embodiment of the invention, 20 ppm of a polypeptide according to the invention reduces the falling number of a flour sample by at least 50%, at least 60%, at least 70%, at least 80% or at least 90%, without the addition of malt flour. In another embodiment, 20 ppm of a polypeptide according to the invention may reduce the falling number of a flour sample with a falling number between 1000 and 1500 to a falling number in the range of 150 to 350, without the addition of malt flour.

In another aspect the present invention relates to a method for improving flour quality, which method comprises adding an effective amount of the polypeptide or the composition according to the invention to flour to reduce the stirring number. In one embodiment of the invention, 20 ppm of a polypeptide according to the invention reduces the stirring number of a flour sample by at least 50%, at least 60%, at least 70%, at least 80% or at least 90%, without the addition of malt flour. In another embodiment, 20 ppm of a polypeptide according to the invention may reduce the stirring number of a flour sample with a stirring number between 1000 and 1500 to a stirring number in the range of 150 to 350, without the addition of malt flour.

In yet another aspect, the present invention relates to a method for improving flour quality, which method comprises adding an effective amount of a polypeptide or a composition according to the invention to flour to improve flour quality leading to improved dough or baked products made from the flour. Improvements are always relative to flour without polypeptide according to the invention. The term "effective amount" is defined herein as an amount of the polypeptide or composition according to the invention that is sufficient for providing a measurable effect on at least one property of interest of the dough and/or baked product. A suitable amount of polypeptide or composition according to the invention is in a range of 0.1-1000 FAU/kg flour. In one embodiment 1-1000 FAU/kg flour is used, in another embodiment 10-900 FAU/kg flour is used. In one embodiment, 1 ppm-80 ppm of an enzyme having an activity in a range of about 10-900 FAU/g is used. Therefore, in another aspect, the present invention relates to a flour comprising a polypeptide according to the invention. A suitable amount of polypeptide or composition according to the invention is in a range of 1.5-15000 SKB/kg flour. In one embodiment 15-15000 SKB/kg flour is used, in another embodiment 150-13500 SKB/kg flour is used. SKB is preferably determined using AACC method 22-01. A flour according to the invention may be used to produce a dough according to the invention. Therefore, in yet another aspect, the present invention relates to a dough prepared from a flour or a pre-mix comprising a polypeptide according to the invention. Therefore, in a further aspect, the invention relates to a dough comprising a polypeptide according to the invention. In one embodiment, the flour of the invention leads to an improved dough, such as a dough with improved machinability due to reduced stickiness. Reduced dough stickiness may be determined by methods known in the art, such as by evaluation by a skilled baker or by using a texture analyser. In one embodiment, reduced dough stickiness is determined in a Warburtons dough stickiness system. Preferably dough stickiness is determined at ambient temperature. Ambient temperature may typically be between 20 and 30 degrees Celcius.

In the context of the present invention, the term 'dough' is defined as a mixture of flour and other ingredients. In the context of the present invention, the term 'dough' is defined as a mixture of flour and dough ingredients. In one embodiment, the dough is firm enough to knead or roll. The dough may be fresh, frozen, prepared or par-baked. The preparation of frozen dough is described by Kulp and Lorenz in Frozen and Refrigerated Doughs and Batters.

Dough is made using dough ingredients, which include without limitation (cereal) flour, a lecithin source including egg, water, salt, sugar, flavours, a fat source including butter, margarine, oil and shortening, baker's yeast, chemical leavening systems such as a combination of an acid (generating compound) and bicarbonate, a protein source including milk, soy flour, oxidants (including ascorbic acid, bromate and Azodicarbonamide (ADA), reducing agents (including L-cysteine), emulsifiers (including mono/di glycerides, monoglycerides such as glycerol monostearate (GMS), sodium stearoyl lactylate (SSL), calcium stearoyl lactylate (CSL), polyglycerol esters of fatty acids (PGE) and diacetyl tartaric acid esters of mono- and diglycerides (DATEM), gums (including guargum and xanthangum), flavours, acids (including citric acid, propionic acid), starch, modified starch, gluten, humectants (including glycerol) and preservatives.

Dough is usually made from basic dough ingredients including (cereal) flour, such as wheat flour or rice flour, water and optionally salt. Cereals include maize, rice, wheat, barley, sorghum, millet, oats, rye, triticale, buckwheat, quinoa, spelt, einkorn, emmer, durum and kamut.

For leavened products, primarily baker's yeast is used next to chemical leavening systems such as a combination of an acid or acid generating compound and bicarbonate.

In the context of the present invention, the term dough includes a batter. A batter is a semi-liquid mixture, being thin enough to drop or pour from a spoon, of one or more flours combined with liquids such as water, milk or eggs used to prepare various foods, including cake. A batter is typically made using flour combined with a liquid source such as water, milk or eggs used to prepare a cake. The dough may be made using a mix including a cake mix, a biscuit mix, a brownie mix, a bread mix, a pancake mix and a crepe mix.

The term dough includes frozen dough, which may also be referred to as refrigerated dough. There are different types of frozen dough; that which is frozen before proofing and that which is frozen after a partial or complete proofing stage. The frozen dough is typically used for manufacturing baked products including without limitation biscuits, breads, bread sticks and croissants.

In one embodiment, a composition according to the invention is added to a dough. The composition according to the invention may be provided in a dry form, to allow easy addition to the dough, but liquid forms are also possible. A liquid form includes without limitation an emulsion, a suspension and a solution. Irrespective of the formulation of the enzyme composition, any additive or additives known to be useful in the art to improve and/or maintain the enzyme's activity, the quality of the dough and/or the baked product may be applied.

Yeast, enzymes and optionally additives are generally added separately from each other to the dough. Enzymes may be added in a dry, e.g. granulated form, in a liquid form or in the form of a paste. Additives are in most cases added in powder form. Suitable additives include oxidants, including ascorbic acid, bromate and Azodicarbonamide (ADA); reducing agents, including L-cysteine; emulsifiers, including lecithin and mono and diglycerides, such as glycerol monostearate (GMS), sodium stearoyl lactylate (SSL), calcium stearoyl lactylate (CSL), polyglycerol esters of fatty acids (PGE) and diacetyl tartaric acid esters of mono- and diglycerides (DATEM); gums, including guargum and xanthan gum; flavours, acids, including citric acid and propionic acid; starch, including modified starch; gluten; humectants, including glycerol; and preservatives.

The preparation of a dough from the dough ingredients is well known in the art and includes mixing of said ingredients and optionally one or more moulding and fermentation steps. A method for preparing a dough comprising the step of combining the polypeptide according to the invention or a composition according to the invention and at least one dough ingredient, is also encompassed by the present invention.

The preparation of baked products from such doughs is also well known in the art and may comprise moulding and shaping and further fermentation of the dough followed by baking at required temperatures and baking times. In one embodiment the invention provides a method to prepare a baked product comprising the step of baking a dough comprising a polypeptide according to the invention. The baking of the dough to produce a baked product may be performed using methods well known in the art. The invention also provides a baked product obtainable according to this method. In one embodiment of the invention, the baked product according to the invention is bread or cake.

Examples of baked products, whether of a white, brown or whole-meal type, which may be advantageously produced by the present invention include bread (in particular white, whole-meal or rye bread), typically in the form of loaves or rolls, French baguette-type bread, pastries, croissants, brioche, panettone, pasta, noodles (boiled or (stir-)fried), pita bread and other flat breads, tortillas, tacos, cakes, pancakes, cookies in particular biscuits, doughnuts, including yeasted doughnuts, bagels, pie crusts, steamed bread, crisp bread, brownies, sheet cakes, snack foods (e.g., pretzels, tortilla chips, fabricated snacks, fabricated potato crisps). The term baked product includes, bread containing from 2 to 30 wt % sugar, fruit containing bread, breakfast cereals, cereal bars, eggless cake, soft rolls and gluten-free bread. Gluten free bread herein and herein after is bread than contains at most 20 ppm gluten. Several grains and starch sources are considered acceptable for a gluten-free diet. Frequently used sources are potatoes, rice and tapioca (derived from cassava). Baked product includes without limitation tin bread, loaves of bread, twists, buns, such as hamburger buns or steamed buns, chapati, rusk, dried steam bun slice, bread crumb, matzos, focaccia, melba toast, zwieback, croutons, soft pretzels, soft and hard bread, bread sticks, yeast leavened and chemically-leavened bread, laminated dough products such as Danish pastry, croissants or puff pastry products, muffins, Danish bagels, confectionery coatings, crackers, wafers, pizza crusts, tortillas, pasta products, crepes, waffles, par-baked products and refrigerated and frozen dough products.

An example of a par-baked product includes, without limitation, partially baked bread that is completed at point of sale or consumption with a short second baking process.

The bread may be white or brown pan bread and may for example be manufactured using a so called American style Sponge and Dough method or an American style Direct method.

The term tortilla herein includes corn tortilla and wheat tortilla. A corn tortilla is a type of thin, flat bread, usually unleavened made from finely ground maize (usually called "corn" in the United States). A flour tortilla is a type of thin, flat bread, usually unleavened, made from finely ground wheat flour. The term tortilla further includes a similar bread from South America called arepa, though arepas are typically much thicker than tortillas. The term tortilla further includes a laobing, a pizza-shaped thick "pancake" from China and an Indian Roti, which is made essentially from wheat flour. A tortilla usually has a round or oval shape and may vary in diameter from about 6 to over 30 cm.

Baked products obtained by using a dough prepared according to the invention are also encompassed by the present invention. All the embodiments which were mentioned above for the flour, with all the preferences mentioned above, also apply to doughs and baked products according to the invention.

In yet another aspect, compositions according to the invention may be used as bread improvers or dough improvers, which are combined with flour to improve functionalities of the bread, dough or of the baked product made from the dough. The improvement is in comparison to a flour which is not combined with a bread or dough improver according to the invention and may be reflected in any functionality of the bread, dough or baked product from the dough, such as increased strength of the dough, increased viscoelasticity of the dough, increased stability of the dough, reduced stickiness of the dough, improved extensibility of the dough, improved machinability of the dough, increased volume of the baked product, improved flavour of the baked product, improved crumb structure of the baked product, improved crumb softness of the baked product, reduced blistering of the baked product, improved crispiness, improved resilience both initial and in particular after storage, reduced hardness after storage or improved anti-staling properties of the baked product.

The term "increased strength of the dough" is defined herein as the property of a dough that has generally more viscoelastic properties and/or requires more work input to mould and shape.

The term "increased viscoelasticity of the dough" is defined herein as the property of a dough which has a higher tendency to regain its original shape after being subjected to a certain physical strain.

The term "increased stability of the dough" is defined herein as the property of a dough that is less susceptible to forming faults as a consequence of mechanical abuse thus better maintaining its shape and volume and is evaluated by the ratio of height: width of a cross section of a loaf after normal and/or extended proof.

The term "reduced stickiness of the dough" is defined herein as the property of a dough that has less tendency to adhere to surfaces, e.g., in the dough production machinery, and is either evaluated empirically by the skilled test baker or measured by a suitable system known in the art, such as Warburtons dough stickiness system. Reduced dough stickiness, also referred to herein as reduced stickiness of the dough, may be determined by methods known in the art, such as by evaluation by a skilled baker or by using a texture analyser. In one embodiment, reduced dough stickiness is determined in a Warburtons dough stickiness system. Preferably dough stickiness is determined at ambient temperature. Ambient temperature may typically be between 20 and 30 degrees Celcius.

Dough stickiness may be evaluated through tactile assessment for example while shaping the dough. Alternatively dough stickiness may be evaluated after shaping the dough, by touching the surface of the shaped dough and sensing how much it sticks to the fingers. If the dough sticks less to the fingers than a reference it is evaluated as having a reduced dough stickiness. Alternatively dough stickiness may be evaluated after cutting the dough, by touching the surface of the freshly cut dough surface and sensing how much it sticks to the fingers. If the dough sticks less to the fingers than a reference it is evaluated as having a reduced dough stickiness. The term "improved extensibility of the dough" is defined herein as the property of a dough that can be subjected to increased strain or stretching without rupture.

The term "improved machinability of the dough" is defined herein as the property of a dough that is generally less sticky and/or more firm and/or more elastic. Consequently there is less fouling of plant equipment and a reduced need for cleaning.

The term "improved crumb structure of the baked product" is defined herein as the property of a baked product with finer cells and/or thinner cell walls in the crumb and/or more uniform/homogenous distribution of cells in the crumb and is usually evaluated visually by the baker or by digital image analysis as known in the art (eg. C-cell, Calibre Control International Ltd, Appleton, Warrington, UK).

The term "improved softness of the baked product" is the opposite of "hardness" and is defined herein as the property of a baked product that is more easily compressed and is evaluated either empirically by the skilled test baker or measured by the use of a texture analyzer known in the art.

The term "reduced blistering of the baked product" is defined herein as a visually determined reduction of blistering on the crust of the baked bread.

The term "improved crispiness" is defined herein as the property of a baked product to give a crispier sensation than a reference product as known in the art, as well as to maintain this crispier perception for a longer time than a reference product. This property can be quantified by measuring a force versus distance curve at a fixed speed in a compression experiment using e.g. a texture analyzer TA-XT Plus (Stable Micro Systems Ltd, Surrey, UK), and obtaining physical parameters from this compression curve, viz. (i) force of the first peak, (ii) distance of the first peak, (iii) the initial slope, (iv) the force of the highest peak, (v) the area under the graph and (vi) the amount of fracture events (force drops larger than a certain preset value). Indications of improved crispness are a higher force of the first peak, a shorter distance of the first peak, a higher initial slope, a higher force of the highest peak, higher area under the graph and a larger number of fracture events. A crispier product should score statistically significantly better on at least two of these parameters as compared to a reference product. In the art, "crispiness" is also referred to as crispness, crunchiness or crustiness, meaning a material with a crispy, crunchy or crusty fracture behaviour.

The term "improved anti-staling properties of the baked product" is defined herein as the properties of a baked product that have a reduced rate of deterioration of quality parameters, e.g. reduced hardness after storage and/or decreased loss of resilience after storage. Anti-staling properties may be demonstrated by a reduced hardness after storage of the baked product. The enzyme composition according to the invention or the pre-mix according to the invention may result in reduced hardness, e.g. in a baked product that is more easily compressed. The hardness of the baked product may be evaluated either empirically by the skilled test baker or measured by the use of a texture analyzer known in the art. The hardness measured within 24 hours after baking is called initial hardness. The hardness measured 24 hours or more after baking is called hardness after storage, and is also a measure for determining shelf life. In case the initial hardness has reduced, it has improved. In case the hardness after storage has reduced, it has improved. Resilience of the baked product is preferably measured by the use of a texture analyzer known in the art. The resilience measured within 24 hours after baking is called initial resilience. The resilience measured 24 hours or more after baking is called resilience after storage, and is also a measure for determining shelf life. Freshly baked product typically gives crumb of high initial resilience but resilience is lost over shelf-life. Improved anti-staling properties may be demonstrated by a reduced loss of resilience over storage.

In yet another aspect, the present invention relates to the use of a polypeptide or composition according to the invention in the brewing industry. In one embodiment, a polypeptide or composition according to the invention is used for the replacement of malt in brewing.

In yet another aspect of the invention, the polypeptide or composition according to the invention may be used for the production of glucose, fructose and maltose syrups; for the production of starch hydrolysates such as maltodextrins; for the production of modified starches; for the modification of starch components in animal feed; in a glue including wall paper paste; in plastic objects made using starch, including plastic bags made from polymerized starch films; or in waste bread reprocessing.

In aspect 1 of the invention a polypeptide according to the invention is a polypeptide which has alpha amylase activity and which has a polypeptide sequence which shows at least 85% identity to amino acids 18 to 495 of SEQ ID No. 1.

In aspect 2 of the invention the polypeptide according to the invention is a polypeptide according to aspect 1 which
  i) when aligned with the alpha-amylase comprising the amino acid sequence as set out in amino acids 18 to 495 of SEQ ID No. 3, comprises at least one substitution of an amino acid residue at one or more positions corresponding to any of positions 22, 46, 48, 50, 52, 64, 65, 80, 84, 89, 91, 94, 109, 111, 126, 143, 155, 158, 161, 166, 168, 170, 171, 173, 174, 177, 194, 196, 197, 198, 199, 201, 203, 208, 209, 210, 238, 245, 249, 262, 263, 277, 280, 286, 287, 301, 303, 310, 323, 326, 331, 332, 335, 338, 346, 353, 364, 370, 372, 381, 382, 384, 388, 394, 396, 397, 402, 406, 408, 409, 422, 423, 425, 429, 434, 443, 450, 454, 455, 456, 463, 465, 474, 483, 484, 487, 490 and 491, wherein said positions are defined with reference to SEQ ID No. 3; or
  ii) has the amino acid sequence as defined under i) and wherein the polypeptide has an increased thermostability as compared with the alpha-amylase as set out in amino acids 18 to 495 of SEQ ID No. 3; or
  iii) has the amino acid sequence as defined under i) and wherein the polypeptide has reduces the stirring number as compared with the alpha-amylase as set out in amino acids 18 to 495 of SEQ ID No. 3; or
  iv) has an amino acid sequence as set out in amino acids 18 to 495 of SEQ ID No. 1.

In aspect 3 of the invention the polypeptide according to the invention is a polypeptide according to aspect 2, wherein the polypeptide has an amino acid sequence which, when aligned with the alpha-amylase comprising the amino acid sequence as set out in amino acids 18 to 495 of SEQ ID No. 3, comprises at least one of the following substitutions:
  D22E, T46A, N48D, A50S, Q52R, D64N, K65H, T80S, A84E, T89D, A91G, D94E, E109S, Y111F, E126A, D143A, K155N, S158N, D161S, F166Y, F168L, Q170T, N171D, E173N, D174N, Q177N, D194R, T196E, K197D, D198S, V199D, K201Q, E203I, V208I, G209K, S210E, K238D, I245V, L249F, V262Y, M263L, N277R, K280Q, M286I, D287S, P301A, S303P, V310I, N323S, A326S, V331A, A332I, I335T, N338S, A346Y, A353S, T364L, P370S, D372T, S381T, A382L, A384K, Y388H, T394S, F396Y, V397L, W402Y, K406Q, D408S, T409N, I422V, V423I, I425V, K429L, D434S, A443T, Q450K, V454I, I455Y, G456T, G463D, D465S, G474S, T483A, E484S, A487S, K490G, I491L wherein the positions are defined with reference to SEQ ID No. 3.

In aspect 4 of the invention a polynucleotide sequence of the invention is a polynucleotide sequence encoding a polypeptide according to any one of aspects 1 to 3.

In aspect 5 of the invention a vector of the invention is a vector comprising a polynucleotide sequence according to aspect 4.

In aspect 6 of the invention the vector of the invention is a vector according to aspect 5 which is an expression vector, wherein the polynucleotide sequence according to aspect 4 is operably linked with at least one regulatory sequence allowing for expression of the polynucleotide sequence in a suitable host cell.

In aspect 7 of the invention the vector of the invention is the vector according to aspect 6, wherein the suitable host cell is an *Aspergillus, Bacillus, Chrysosporium, Escherichia, Kluyveromyces, Penicillium, Pseudomonas, Saccharomyces, Streptomyces* or *Talaromyces* species, preferably a *Bacillus subtilis, Bacillus amyloliquefaciens, Bacillus licheniformis, Escherichia coli, Aspergillus niger* or *Aspergillus oryzae* species.

In aspect 8 of the invention a recombinant host cell of the invention is a recombinant host cell comprising the polynucleotide sequence according to aspect 4 or comprising the vector according to any one of aspects 5 to 7. In a further aspect the recombinant host cell is an *Aspergillus, Bacillus, Chrysosporium, Escherichia, Kluyveromyces, Penicillium, Pseudomonas, Saccharomyces, Streptomyces* or *Talaromyces* species, preferably a *Bacillus subtilis, Bacillus amyloliquefaciens, Bacillus licheniformis, Escherichia coli, Aspergillus niger* or *Aspergillus oryzae* species.

In aspect 9 of the invention the recombinant host cell is the recombinant host cell according to aspect 8 capable of expressing or over-expressing said polynucleotide sequence or said vector.

In aspect 10 of the invention a method of the invention is a method for preparing a polynucleotide sequence according to aspect 4 or the vector according to any one of aspects 5 to 7 comprising the steps of culturing a host cell transformed with said polynucleotide sequence or said vector and isolating said polynucleotide sequence or said vector from said host cell. In a further aspect of the invention a method of the invention is a method for preparing a polynucleotide sequence according to aspect 4 or the vector according to any one of aspects 5 to 7 comprising the steps of culturing a host cell transformed with said polynucleotide sequence or said vector and optionally isolating said polynucleotide sequence or said vector from said host cell.

In aspect 11 of the invention a method of the invention is a method for preparing the polypeptide according to any one of aspects 1 to 3 comprising cultivating a recombinant host cell according to aspect 8 or 9 under conditions which allow for expression of the polynucleotide sequence according to aspect 4 or the vector according to aspects 5 to 7 and, optionally, recovering the encoded polypeptide from the cell or culture medium.

In aspect 12 of the invention a use of the invention is use of the polypeptide according to any one of aspects 1 to 3 in food manufacturing, in particular in the baking or brewing industry.

In aspect 13 of the invention a use of the invention is use according to aspect 12 in the manufacture of a baked product.

In aspect 14 of the invention a composition of the invention is a composition comprising a polypeptide according to any one of aspects 1 to 3.

According to another aspect, the invention relates to a composition comprising a polypeptide according to the invention and a dough ingredient and an additional enzyme.

According to another aspect, the invention relates to a composition comprising a polypeptide according to the invention and a dough ingredient.

According to another aspect, the invention relates to a composition comprising a polypeptide according to the invention and an additional enzyme.

In aspect 15 of the invention the composition of the invention is a composition according to aspect 14, wherein the composition comprises one or more components selected from the group consisting of milk powder, gluten, granulated fat, an additional enzyme, an amino acid, a salt, an oxidant such as ascorbic acid, bromate and azodicarbonamide, a reducing agent such as L-cysteine, an emulsifier such as lecithine, mono-glycerides, di-glycerides, glycerol monostearate, sodium stearoyl lactylate, calcium stearoyl lactylate, polyglycerol esters of fatty acids and diacetyl tartaric acid esters of mono- and diglycerides, gums such as guar gum and xanthan gum, flavours, acids such as citric acid and propionic acid, starch, modified starch, gluten, humectants such as glycerol, and preservatives.

In aspect 16 of the invention the composition of the invention is a composition according to aspect 14 or 15, wherein the additional enzyme is lipolytic enzyme, preferably a phospholipase.

In aspect 17 of the invention a premix of the invention is a premix or a flour comprising a polypeptide according to any one of aspects 1 to 3.

In aspect 18 of the invention a dough according to the invention comprises the polypeptide according to any one of aspects 1 to 3.

In aspect 19 of the invention the of the invention is a dough according to aspect 18, wherein the dough is a dough prepared using a premix or flour according to aspect 17.

In aspect 20 of the invention a baked product of the invention is a baked product prepared using a premix or flour according to aspect 17 or using a dough according to aspect 18 or 19.

In aspect 21 of the invention a method of the invention is a method for preparing a dough comprising the step of combining the polypeptide according to any one of aspects 1 to 3 or a composition according to aspects 14 to 16 and at least one dough ingredient.

In aspect 22 of the invention a method of the invention is a method for preparing a baked product comprising the step of baking the dough according to aspect 18 or 19.

In aspect 23 of the invention a use of the invention is the use of a polypeptide according to any one of aspects 1 to 3 or a composition according to aspect 14 or 15 for correcting flour.

In aspect 24 of the invention a use of the invention is the use according to aspect 23, wherein a polypeptide according to any one of aspects 1 to 3 is used to influence, in particular to decrease, the falling number or the stirring number of flour.

In aspect 25 of the invention a method of the invention is a method for improving flour quality, which method comprises adding an effective amount of a polypeptide according to any one of aspects 1 to 3 or a composition according to aspects 14 to 16 to flour.

In aspect 26 of the invention a method of the invention is a method according to aspect 25, wherein a polypeptide according to any one of aspects 1 to 3 or a composition according to aspects 14 to 16 is added to flour to improve the machinability of dough made from the flour, to reduce the stickiness of dough made from the flour or to improve the anti-staling properties of a baked product made from the dough.

In aspect 27 of the invention the dough of the invention is a dough according to aspect 18 with improved machinability or reduced stickiness compared to a dough not comprising a polypeptide according to any one of aspects 1 to 3.

In aspect 28 of the invention the composition of the invention comprises a polypeptide according to according to any one of aspects 1 to 3, a dough ingredient and/or an additional enzyme.

EXAMPLES

Materials and Methods
General Molecular Biology Techniques

General molecular biology techniques are known to a skilled person in the art (see: Sambrook & Russell, Molecular Cloning: A Laboratory Manual, 3rd Ed., CSHL Press, Cold Spring Harbor, N.Y., 200). Expression cassettes can be improved through several methods as detailed for example in WO 2005/100573, WO2006/077258, WO 2006/092396 or WO2008/000632.

Cloning Vector

For cloning of AMY1 encoding nucleotide sequence and expression of AMY1 polypeptide according to the invention in *Aspergillus* the pGBTOP-16 vector is used. The pGBTOP-16 vector is derived from the pGBTOP-12 vector described in WO 2011/009700. In addition to pGBTOP-12, it contains the ccdB gene from *E. coli* for positive selection for presence of an insert between the EcoRI and PacI cloning sites. The PacI restriction site replaces the SnaBI restriction site present in pGBTOP-12. This vector is linearized by NotI digestion prior to transformation.

Alpha Amylase Activity Measurements

Alpha amylase activity was determined at different temperatures. Herein Act37 means, Alpha amylase activity determined at 37 degrees C., Act30 means Alpha amylase activity determined at 30 degrees C. and Act25 means Alpha amylase activity determined at 25 degrees C. If no reference to temperature is made the Alpha amylase activity was determined at 37 degrees C. Alpha amylase activity at 37 degrees is now described in detail. The Act25 and Act30 values were determined in the same manner but at the temperature indicated i.e. at 25 degrees C. and at 30 degrees C. respectively. Alpha amylase activity was determined at 37 degrees C. and pH 5.2 using a non-reducing-end blocked p-nitrophenyl maltoheptaoside substrate (=BPNPG7) combined with excess levels of thermostable α-glucosidase and amyloglucosidase (Megazyme Ceralpha kit). Hydrolysis of BPNPG7 substrate by endo-acting α-amylase activity resulted in p-nitrophenyl maltosaccharide fragments. Excess quantities of α-glucosidase present in the reaction mixture resulted in instantaneous and quantitative hydrolysis of this p-nitrophenyl maltosaccharide fragment resulting into glucose and free p-nitrophenol. The reaction was terminated (and colour developed) by the addition of an alkaline solution. The absorbance at a wavelength of 405 nm was determined and is a measure for enzymatic activity. Activity was calculated through a molecular extinction coefficient determination through a calibration with a paranitrophenol.solution of known concentration. Sample dilutions were prepared in 50 mM malic acid buffer pH 5.2, containing 50 mM NaCl, 2 mM CaCl2 and 0.05% BSA, in a range of 0.03 to 0.15 U/ml Ceralpha assay reagent from a Megazyme α-amylase kit test (Ceralpha, R-CAAR-4) was dissolved in 10 ml water, to which 8 ml of the malic acid buffer was added. After preheating 540 µl of this substrate in 2 ml Eppendorf vials in a water bath at the indicated temperatures, 60 µl of sample dilution was added to start the incubation. The reaction was terminated after 7 minutes and 5 seconds by addition of 450 µl of a 170 mM Tris solution. Samples were stored on ice until the absorbance at 405 nm was recorded. Sample blanks are measured by reversing the pipetting order: first stop reagent, then sample and substrate. Activity was calculated from the delta absorbance between sample and blank incubations using the para-nitrophenol molar extinction coefficient determined in the same series according to:

$$U/g\ sample = [1000 \times (Abs(sample) - Abs(blank))/(\epsilon pNP \times 7.05) \times 175/10 \times Df)]/W$$

where:
1000=factor from mmol to µmol
$Abs_{sample} - Abs_{blank}$=absorbance in sample incubation corrected for absorbance in blank incubation
εpNP=Molar Extinction Coefficient of para-nitro-phenol [L·mol-1·cm-1]
7.05=Incubation time [min]
175=assay final volume [µL]
10=sample volume [µL]
Df=Dilution factor
W=sample weight [g]
U=µmol/min Thermostability Test and Residual Activity Thermostability analyses were performed by measuring the alpha amylase activity of the sample before and after 15 min incubation at elevated temperature at pH 5.2. Subsequently, residual activity was determined. Residual activity is defined as the ratio of the activity at 37 degrees C. after incubation at elevated temperature to the activity at 37 degrees C. without a heating step.

$$\text{Residual Activity} = \frac{\text{Activity at 37 degrees C. after 15 min elevated } T}{\text{Activity at 37 degrees C. without elevated } T} \times 100\%$$

Stirring Number Test

The stirring number test is performed using a Rapid Visco Analyzer (RVA). As in the falling number test (S. Hagberg (1960) Cereal Chem 37: 218, and see the detailed description of this application), a flour slurry is prepared, by mixing 3.5 g flour (Kolibri flour (Meneba, Netherlands) with 25 ml H$_2$O The sample is placed in the RVA and quickly heated up to 95° C. The sample is stirred in the RVA, while the viscosity is measured. The stirring number is defined as the viscosity measured after 180 seconds. Alpha-amylase activity decreases the viscosity and leads to a lower stirring number. Samples with little alpha-amylase activity will have a high stirring number. Since the stirring number test is based on the same physical principle as the falling number test, the falling number and the stirring number of a sample are correlated.

The stirring number test was performed using a Rapid Visco Analyzer (RVA) according to the RVA™ stirring number method (RVA 02.04) from Perten.

Example 1

Preparation of a Polypeptide According to the Invention

A polypeptide according to the invention, further referred to as AMY 1, is comprised in SEQ ID No. 1. This sequence consists of a signal sequence of 17 amino acids for efficient secretion and a deduced mature polypeptide sequence of 478 amino acids (position 18-495 from SEQ ID No. 1). The signal sequence used for secretion of the AMY1 polypeptide is the pectin methyl esterase (pmeA) signal sequence (in position 1-17 in SEQ ID NO.1). The secreted (mature) AMY1 polypeptide of the invention is shown as position 18-495 of SEQ ID No. 1. To be able to express the polypeptide, a codon-adapted DNA sequence for expression of the polypeptide protein in *Aspergillus niger* was designed containing additional restriction sites for subcloning in an *Aspergillus* expression vector. Codon adaptation was performed as described in WO 2008/000632. The codon optimized DNA sequence for *A. niger* of the gene encoding the polypeptide of SEQ ID. NO. 1 is shown in SEQ ID No. 2.

The translational initiation sequence of the glucoamylase glaA promoter was modified into 5'-CACCGTCAAA ATG-3' and an optimal translational termination sequence 5'-TAAA-3' was used in the generation of the expression construct (as also detailed in WO2006/077258). A DNA fragment containing a.o. part of the glucoamylase promoter, the translational initiation sequence, the codon-adapted AMY1 encoding gene and translational termination sequence was synthesized completely by DNA2.0 (California, USA), purified and digested with EcoRI and PacI. The pGBTOP-16 vector (FIG. 4) was linearized by EcoRI/PacI digestion and the synthetic DNA fragment was cloned into the pGBTOP-16 vector resulting in a pGBTOP-AMY1 expression vector.

Subsequently, *A. niger* GBA 307 (ΔglaA, ΔpepA, ΔhdfA, adapted BamHI amplicon, ΔamyBII, ΔamyBI, ΔamyA, ΔoahA, alpha-amylase and glucoamylase negative strain) was transformed with linearized pGBTOP-AMY1 expression vector by NotI-digestion, in a co-transformation protocol with linearized pGBAAS-4, with strain and methods as described in WO 2011/009700 and references therein, and selected on acetamide containing media and colony purified according to standard procedures. Transformation and selection was performed as described in WO 98/46772 and WO 99/32617. Strains containing the AMY1 gene were selected via PCR with primers specific for the AMY1 gene to verify presence of the AMY1 expression cassette. A single transformant was selected, named AMY1, and further replicaplated to obtain a single strain inoculum.

For fermentation and isolation of the polypeptide, fresh *A. niger* AMY1 spores were prepared. Shake flasks with 20 ml Fermentation medium 1 (10% w/v Corn Steep Solids (Roquette), 1% w/v glucose.$H_2O$, 0.1% w/v $NaH_2PO_4.H_2O$, 0.05% w/v $MgSO_4.7H_2O$, 0.025% w/v Basildon, pH 5.8: sterilized for 10 minutes at 110° C. after which 200 μl of a sterile solution containing 5000 IU/ml penicillin and 5 mg/ml Streptomycin was added to each flask after cooling to room temperature) in 100 ml shake flasks with baffle were inoculated with at least $2*10^6$ spores. These pre-cultures were incubated at 34° C. and 170 rpm for 18-24 hours.

From these pre-cultures, 5 ml was used for inoculation of shake flasks with 100 mL Fermentation medium 2 (15% w/v maltose, 6% w/v bacto-soytone, 1.5% w/v $(NH_4)_2SO_4$, 0.1% w/v $NaH_2PO_4.H_2O$, 0.1% w/v $MgSO_4.7H_2O$, 0.1% w/v L-arginine, 0.5% w/v $CaCl_2$, 8‰ w/v Tween-80, 2‰ w/v Basildon, 2% w/v MES pH 6.2: sterilized for 20 minutes at 120° C. after which 1 ml of a sterile solution containing 5000 IU/ml penicillin and 5 mg/ml Streptomycin was added to each flask after cooling to room temperature) in a 500 mL shake flask size and shaken at 34° C. and 170 rpm.

After four days of cultivation, cell-free supernatants were obtained by centrifugation of the fermentation broth at 4000 rpm for 15 minutes at 4° C. The supernatant was sterile filtrated over a 0.2 μm (bottle-top) filter with suction to remove all fungal material solids and stored at −20° C. until further use.

Example 2

Thermostability Testing of AMY1 Polypeptide According to the Invention. (Residual Activity)

Thermostability analyses of AMY1 polypeptide was performed by measuring Residual alpha amylase activity of the samples as described in Materials & Methods. *A. niger* alpha amylase (as set out in amino acids 18 to 495 of FIG. 3, as set out in amino acids 18 to 495 of SEQ ID No. 3) was used as a reference. All samples were incubated at elevated temperatures in the range of 51 to 70 degrees C. at pH 5.2. The results are depicted in Table 1 and FIG. 5 and show that AMY1 is significantly more thermostable than *A. niger* alpha amylase (ANA). After 15 min at 54.6 degrees C. AMY1 still has at least 100% of its alpha amylase activity, compared to less than 50% for the *A. niger* alpha amylase (ANA).

TABLE 1

Residual alpha amylase activity at elevated temperature

| T (° C.) (15 min, pH 5.2) | ANA | AMY1 |
|---|---|---|
| 51 | 79% | 104% |
| 52.9 | 66% | 106% |
| 54.6 | 47% | 104% |
| 56.6 | 24% | 101% |
| 59.5 | 5% | 96% |
| 61.7 | *1%* | 92% |
| 63.7 | *1%* | 86% |
| 66 | *1%* | n.d. |
| 68 | n.d. | 48% |
| 70 | n.d. | 22% |
| 71.1 | n.d. | 8% |
| 72.1 | n.d. | *3%* |
| 73.2 | n.d. | *1%* |

Values outside official assay measuring range are indicated in italics
n.d.: not determined Example 3

Alpha Amylase Activity at Different Temperatures (Relative Activity)

Alpha amylase activity at different temperatures was measured as described above and the Relative Activity was determined, whereby the activity at 37 degrees C. was set at 100%. Results are presented in Table 2 and show that AMY1 has lower relative alpha amylase activity than *A. niger* alpha amylase (ANA) at 25 and 30 degrees C. The Act25/Act37 ratio for AMY1 is 40% (versus 56% for *A. niger* alpha amylase) and the Act30/Act37 ratio is 60% for AMY1 (versus 77% for *A. niger* alpha amylase).

TABLE 2

Alpha amylase activity at different temperatures
(Relative Activity, with the activity at 37 degrees C. set at 100%).

| ratio | ANA | AMY1 |
|---|---|---|
| Act25/Act37 ratio | 56% | 40% |
| Act30/Act37 ratio | 77% | 60% |

Example 4

Performance in the Stirring Number Test

AMY1 polypeptide according to the invention from Example 1 was tested in a stirring number test performed as described in Materials & Methods and compared to the other samples mentioned in Table 3.

TABLE 3

| Sample | |
|---|---|
| Bakezyme P500 | Composition containing *A. oryzae* alpha amylase, DSM, the Netherlands. |
| Ban 800 | Composition containing *B. amyloliquefaciens* thermostable alpha amylase, Novozymes, USA. |
| ANA | *A. niger* fungal alpha amylase |
| AMY1 | Polypeptide according to the invention |

Bakezyme P500 is also referred to herein as BzP500.

Samples were included at two levels of activity (in FAUs) corresponding to 20 ppm and 100 ppm of Bakezyme P500 (DSM, Delft, the Netherlands). Each enzyme and dose was tested in duplicate. Bakezyme P500 and Ban 800 (Novozymes, USA) were included as additional controls, both at 20 ppm. Bakezyme P500 is expected to behave identically to *A. niger* fungal amylase enzyme, since the amino acid sequence of the alpha amylase in Bakezyme P500 is identical to the amino acid sequence of *A. niger* fungal amylase. Ban 800 is a thermostable alpha-amylase from *Bacillus amyloliquefaciens*, which is expected to have a clear effect on the stirring number.

Figure 6:
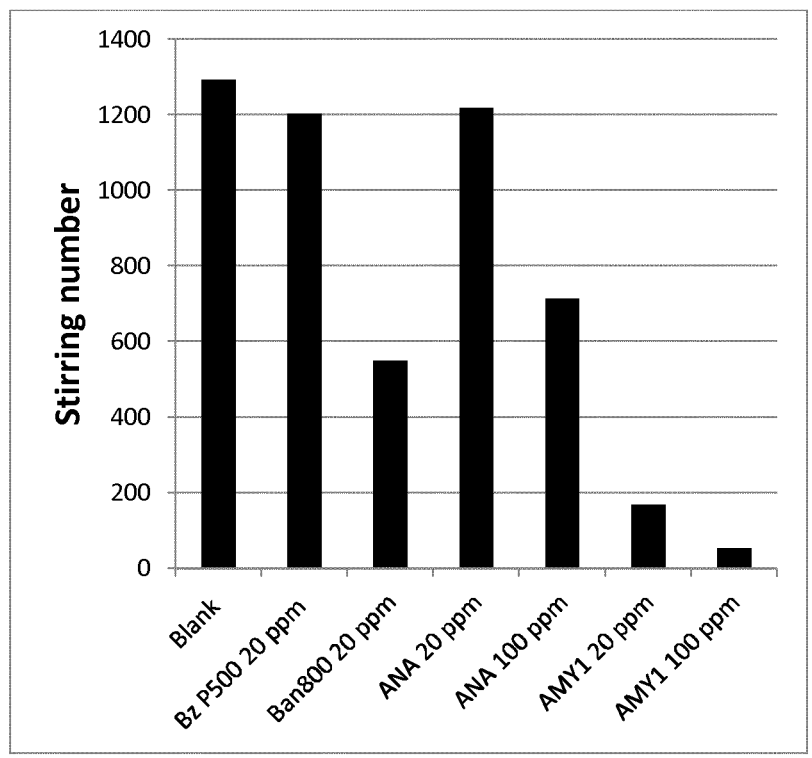
FIG. 6. Effect of AMY1 polypeptide according to the invention on the stirring number.

FIG. 6 shows that the Ban 800 sample indeed clearly lowers the stirring number at 20 ppm, whereas the P500 and the *A. niger* fungal amylase samples only do so to a very limited extent. AMY1 reduces the stirring number from approximately 1300 for the blank to below 200 when added at 20 ppm. At higher doses the polypeptide according to the invention lowers the stirring number even further (Table 4).

TABLE 4

Effect on stirring number

| Sample | Stirring number |
|---|---|
| Blank | 1293 |
| Bz P500 20 ppm | 1205 |
| Ban800 20 ppm | 550 |
| ANA 20 ppm | 1219 |
| ANA 100 ppm | 714 |
| AMY1 (20 ppm) | 169 |
| AMY1 (100 ppm) | 53 |

Figure 7:
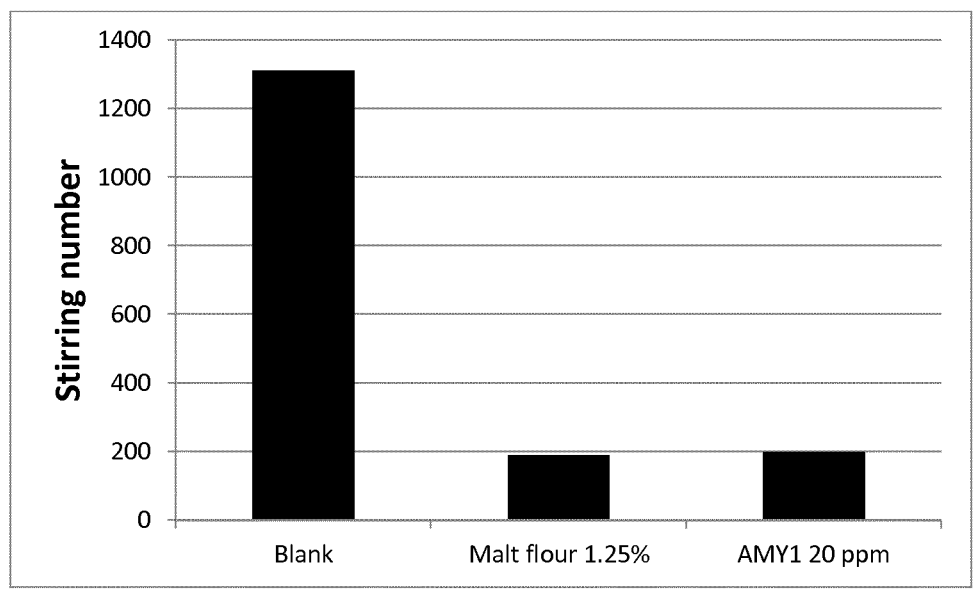
FIG. 7. Effect on the stirring number of AMY1 polypeptide according to the invention compared to malt flour.

The effect of the AMY1 sample on the stirring number was also compared with different levels of malt flour (Paniflour, Belgium) addition. It was found that 20 ppm of AMY1 has similar effect on the stirring number as 1.25% of malt flour added to the flour (FIG. 7 and Table 5).

TABLE 5

Effect on stirring number

| Sample | Stirring number |
|---|---|
| Blank | 1314 |
| Malt flour 1.25% | 191 |
| AMY1 20 ppm | 200 |

Baking tests showed that the functionalities of the bread produced from the flour with AMY1 were comparable to the control.

Example 5

Performance in the Stirring Number Test

AMY1 polypeptide according to the invention from Example 1 was tested in a stirring number test performed as described in Materials & Methods (using a Rapid Visco Analyzer (RVA) according to the RVA™ stirring number method (RVA 02.04) from Perten) and compared to the other samples mentioned in Table 3.

TABLE 6

| Sample | |
|---|---|
| Bakezyme P500 | Composition containing *A. oryzae* alpha amylase, DSM, the Netherlands. |
| Ban 800 | Composition containing *B. amyloliquefaciens* thermostable alpha amylase, Novozymes, USA. |
| ANA | *A. niger* fungal alpha amylase |
| AMY1 | Polypeptide according to the invention |

Bakezyme P500 is also referred to herein as BzP500.

Samples were included at two levels of activity (using the Alpha amylase activity measurement Act37 as described herein) corresponding to 20 ppm and 100 ppm of Bakezyme P500 (DSM, Delft, the Netherlands). Each enzyme and dose was tested in duplicate. Bakezyme P500 and Ban 800 (Novozymes, USA) were included as additional controls, both at 20 ppm. Bakezyme P500 is expected to behave identically to *A. niger* fungal amylase enzyme, since the amino acid sequence of the alpha amylase in Bakezyme P500 is identical to the amino acid sequence of *A. niger* fungal amylase. Ban 800 is a thermostable alpha-amylase from *Bacillus amyloliquefaciens*, which is expected to have a clear effect on the stirring number.

FIG. 6 shows that the Ban 800 sample indeed clearly lowers the stirring number at 20 ppm, whereas the P500 and the *A. niger* fungal amylase samples only do so to a very limited extent. AMY1 reduces the stirring number from approximately 1300 for the blank to below 200 when added at 20 ppm. At higher doses the polypeptide according to the invention lowers the stirring number even further (Table 7).

TABLE 7

Effect on stirring number

| Sample | Stirring number (cP) |
|---|---|
| Blank | 1293 |
| Bz P500 20 ppm | 1205 |
| Ban800 20 ppm | 550 |
| ANA 20 ppm | 1219 |
| ANA 100 ppm | 714 |

TABLE 7-continued

Effect on stirring number

| Sample | Stirring number (cP) |
|---|---|
| AMY1 (20 ppm) | 169 |
| AMY1 (100 ppm) | 53 |

The effect of the AMY1 sample on the stirring number was also compared with different levels of malt flour (Paniflour, Belgium) addition. It was found that 20 ppm of AMY1 has similar effect on the stirring number as 1.25% of malt flour added to the flour (FIG. 7 and Table 8).

TABLE 8

Effect on stirring number

| Sample | Stirring number (cP) |
|---|---|
| Blank | 1314 |
| Malt flour 1.25% | 191 |
| AMY1 20 ppm | 200 |

Baking tests showed that the functionalities of the bread produced from the flour with AMY1 were comparable to the control.

Example 6

The AMY1 polypeptide from Example 1 was evaluated in a dough stickiness test, using a tin bread recipe. 3000 g of flour (2400 g Kolibri and 600 g Ibis), 72 g compressed yeast, 48 g salt, 20 ppm ascorbic acid, 15 ppm Bakezyme HSP6000 (hemicellulase) and 58% water was mixed in a Diosna mixer at speed 1 for 400 revolutions and speed 2 for 1560 revolutions to a final dough temperature of 27° C. Bakezyme P500 and cell-free supernatant containing AMY1 polypeptide were added to the flour at levels of activity (using the Alpha amylase activity measurement Act37 as described herein) corresponding to 5-20 ppm of Bakezyme P500. Dough was removed from the mixer and stickiness was evaluated through tactile assessment by skilled bakers. Dough stickiness was evaluated immediately after mixing and during shaping of the dough. The results are described in table 9. In table 9 it can be seen that AMY1 can be added in higher levels than Bakezyme P500 before causing dough stickiness.

TABLE 9

Dough stickiness assessment at about 26 degrees Celsius.

| | 5 ppm | 10 ppm | 15 ppm | 20 ppm |
|---|---|---|---|---|
| Bakezyme P500 | Not sticky | Somewhat sticky | Very sticky | Very sticky |
| AMY1 | Not sticky | Not sticky | Somewhat sticky | Very sticky |

Bakezyme HSP 6000 BG: Hemicellulase form *Aspergillus Niger*, DSM, the Netherlands.
Bakezyme P500: alpha-amylase from *Aspergillus oryzae*, DSM, the Netherlands.
Not sticky: dough does not stick more to fingers when touched than the reference dough.
Somewhat sticky: dough sticks a little bit more to fingers when touched than the reference dough.
Very sticky: dough sticks a lot more to fingers when touched than the reference dough.

The reference dough was produced as described above using: 3000 g of flour (2400 g Kolibri and 600 g Ibis), 72 g compressed yeast, 48 g salt, 20 ppm ascorbic acid, 15 ppm Bakezyme HSP6000 (hemicellulase) and 58% water was mixed in a Diosna mixer at speed 1 for 400 revolutions and speed 2 for 1560 revolutions to a final dough temperature of 27° C.

The invention claimed is:

1. A polypeptide which has alpha amylase activity and which has a polypeptide sequence which has at least 90% sequence identity to amino acids 18-495 of SEQ ID NO:1.

2. A polynucleotide sequence encoding the polypeptide according to claim 1.

3. A vector comprising the polynucleotide sequence according to claim 2.

4. A recombinant host cell comprising the polynucleotide sequence according to claim 2 or comprising a vector comprising said sequence.

5. A product comprising the polypeptide according to claim 1.

6. A composition comprising the polypeptide according to claim 1.

7. A composition comprising the polypeptide according to claim 1, a dough ingredient, and/or an additional enzyme.

8. A premix or a flour comprising the polypeptide according to claim 1.

9. A dough comprising the polypeptide according to claim 1.

10. A method for preparing a dough comprising combining the polypeptide according to claim 1, and at least one dough ingredient.

11. A method for preparing a baked product comprising baking the dough according to claim 9.

12. A product comprising the polypeptide according to claim 1 or a composition thereof for correcting flour.

13. The product according to claim 12, wherein the polypeptide according to claim 1 is used to influence, optionally to decrease, the falling number or the stirring number of flour.

14. A method for improving flour quality, which method comprises adding an effective amount of the polypeptide according to claim 1 or a composition thereof to flour.

15. A method according to claim 14, wherein the polypeptide according to claim 1 or a composition thereof is added to flour to improve the machinability of dough made from the flour, to reduce the stickiness of dough made from the flour and/or to improve the anti-staling properties of a baked product made from the dough.

16. A polypeptide which has alpha amylase activity and which has at least 95% sequence identity to amino acids 18-495 of SEQ ID NO:1.

* * * * *